US012559484B2

(12) United States Patent
Zhou et al.

(10) Patent No.: US 12,559,484 B2
(45) Date of Patent: Feb. 24, 2026

(54) ROUTE FOR CONSTRUCTING CHIRAL FRAGMENT OF FEZOLINETANT, INTERMEDIATE THEREOF, AND PREPARATION METHOD THEREFOR

(71) Applicant: SHENZHEN HWAGEN PHARMACEUTICAL CO., LTD., Guangdong (CN)

(72) Inventors: Zhangtao Zhou, Guangdong (CN); Zhining Huang, Guangdong (CN); Weiping Ye, Guangdong (CN); Xunqing Dong, Guangdong (CN); Zhen Liu, Guangdong (CN); Huazheng Ou, Guangdong (CN); Xu Deng, Guangdong (CN)

(73) Assignee: SHENZHEN HWAGEN PHARMACEUTICAL CO., LTD., Shenzhen (CN)

( * ) Notice: Subject to any disclaimer, the term of this patent is extended or adjusted under 35 U.S.C. 154(b) by 0 days.

(21) Appl. No.: 19/258,335

(22) Filed: Jul. 2, 2025

(65) Prior Publication Data

US 2026/0015345 A1 Jan. 15, 2026

(30) Foreign Application Priority Data

Jul. 11, 2024 (CN) ......................... 202410929480.3

(51) Int. Cl.
*C07D 417/04* (2006.01)
*C07D 285/08* (2006.01)
*C07D 487/04* (2006.01)

(52) U.S. Cl.
CPC ......... *C07D 417/04* (2013.01); *C07D 285/08* (2013.01); *C07D 487/04* (2013.01)

(58) Field of Classification Search
CPC .................................................... C07D 417/04
See application file for complete search history.

(56) References Cited

U.S. PATENT DOCUMENTS 9,422,299 B2 * 8/2016 Hoveyda ................. A61P 15/12

FOREIGN PATENT DOCUMENTS

| | | |
|---|---|---|
| CN | 1207095 A | 2/1999 |
| CN | 103906750 A | 7/2014 |
| CN | 105229008 A | 1/2016 |
| CN | 107427497 A | 12/2017 |

(Continued)

OTHER PUBLICATIONS

Bartlett "Exploiting Chemical Diversity for Drug Discovery" Edited by Paul A Bartlett and Michael Entzeroth, The Royal Society of Chemistry, 2006, pp. 113-118.*

(Continued)

*Primary Examiner* — Nizal S Chandrakumar
(74) *Attorney, Agent, or Firm* — Rothwell, Figg, Ernst & Manbeck, P.C.

(57) ABSTRACT

A route for constructing chiral fragment of fezolinetant, an intermediate thereof, and a preparation method therefor are disclosed, which relates to the technical field of organic synthesis and preparation of active pharmaceutical ingredient intermediates. The route for constructing chiral fragment of fezolinetant, the intermediate thereof (compounds of Formula G, Formula H, Formula I, and Formula J), and the preparation method therefor provided by the present disclosure are shown in the following synthesis route. The present disclosure provides a novel route for synthesizing a key intermediate (intermediate A0) of Fezolinetant. Starting materials are readily available, chemical reaction conditions of each step are mild, and chiral purity of each intermediate is high, which is conducive to improving chiral purity of the product.

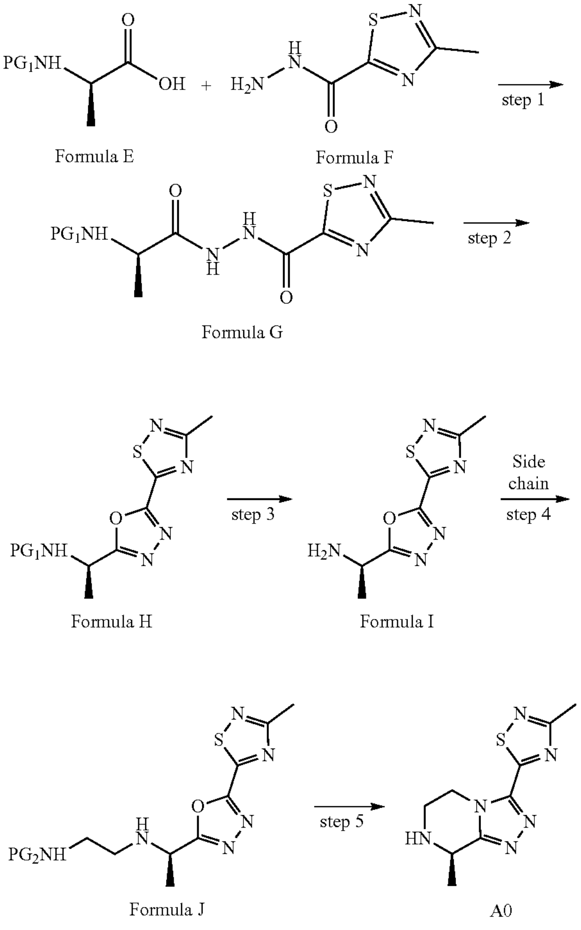

Formula E Formula F Formula G Formula H Formula I Formula J A0

3 Claims, 11 Drawing Sheets

(56) References Cited

FOREIGN PATENT DOCUMENTS

| | | | |
|---|---|---|---|
| CN | 117510506 | A | 2/2024 |
| CN | 117551104 | A | 2/2024 |
| CN | 118290429 | A | 7/2024 |
| RU | 2490271 | C1 | 8/2013 |
| WO | 2011121137 | A1 | 10/2011 |
| WO | 2020211798 | A1 | 10/2020 |

OTHER PUBLICATIONS

"Find ETDs Home » Thesis Resources » Find ETDs" Online: "https://ndltd.org/thesis-resources/find-etds/" Accessed Jan. 31, 2023.*

Irwin "ZINC—A Free Database of Commercially Available Compounds for Virtual Screening" J. Chem. Inf. Model. 2005, 45, 177-182.*

Kim "PubChem in 2021: new data content and improved web interfaces" Nucleic Acids Research, 2021, vol. 49, Database issue Published online Nov. 5, 2020.*

STN Registry/Zregistry (CAS Registrysm) Sep. 2016 2 pages.*

CAS. "RN: 2871414-92-3" Registry (STN) Dec. 19, 2022 (Dec. 19, 2022), p. 1.

International Search Report and Written Opinion dated Mar. 17, 2025 issued in PCT Application No. PCT/CN2024/106188 with English translation (7 pages).

* cited by examiner

| Integration Results | | | | | | | | |
|---|---|---|---|---|---|---|---|---|
| No. | Peak Name | Retention Time min | Area mAU*min | Height mAU | Relative Area % | Resolution USP | Plates USP | Asymmetry USP |
| 1 | | 8.607 | 2.179 | 11.180 | 0.804 | 2.42 | 13226 | 1.31 |
| 2 | | 9.420 | 268.893 | 1107.333 | 99.196 | n.a. | 10244 | 1.44 |
| **Total:** | | | **271.072** | **1118.514** | **100.00** | | | |

Integration Results

| No. | Peak Name | Retention Time min | Area mAU*min | Height mAU | Relative Area % | Resolution USP | Plates USP | Asymmetry USP |
|---|---|---|---|---|---|---|---|---|
| 1 | | 6.700 | 227.937 | 1407.897 | 99.864 | 8.15 | 11460 | 1.28 |
| 2 | | 9.470 | 0.310 | 1.199 | 0.136 | n.a. | 7795 | 1.27 |
| **Total:** | | | **228.247** | **1409.096** | **100.00** | | | |

ROUTE FOR CONSTRUCTING CHIRAL FRAGMENT OF FEZOLINETANT, INTERMEDIATE THEREOF, AND PREPARATION METHOD THEREFOR

CROSS-REFERENCE TO RELATED APPLICATION

This application is based on and claims the benefit of priority from Chinese Patent Application No. 202410929480.3, filed on Jul. 11, 2024, the entirety of which is incorporated by reference herein.

TECHNICAL FIELD

The present disclosure relates to the technical field of organic synthesis and preparation of active pharmaceutical ingredient intermediates, in particular to a route for constructing chiral fragment of fezolinetant, an intermediate thereof, and a preparation method therefor.

BACKGROUND

Vasomotor symptoms (VMS) are characteristic symptoms caused by unstable vasoconstriction due to a decreased or fluctuating estrogen level after menopause, mainly including hot flashes and/or excessive sweating. VMS may seriously affect patients' sense of physical comfort and sleep quality, and in severe cases, will last for five years or longer, causing great distress to women's personal health, workplace jobs, and even their families. Therefore, effective treatments for alleviating these symptoms are urgently needed. VMS have a high incidence during menopause and are also the most common menopausal symptoms for which women seek treatment.

At present, the main treatment for VMS worldwide is hormone replacement therapy (HRT), including estrogen-only and estrogen-progestogen sequential therapy. Multiple studies have shown that HRT can significantly alleviate patient symptoms and is currently the most effective treatment method. However, the long-term use of HRT may increase the risk of venous thromboembolism. Therefore, patients with a high risk of coronary heart disease, stroke, venous thromboembolism, and a history of hormone dependent cancer or illness need to avoid HRT. In addition, the long-term concept of "hormone aversion" further limits the use of HRT.

The small molecule oral drug Fezolinetant with a molecular structural formula as follows selectively targets neurokinin 3 (NK3) receptor, blocks the binding of NK3 to Kisspeptin/neurokinin/dynorphin (KNDy) neurons via binding to NK3 receptor, so as to regulate activity of the neurons in the thermoregulatory center (hypothalamus) of the brain, and to reduce the frequency and severity of menopausal related moderate to severe VMS.

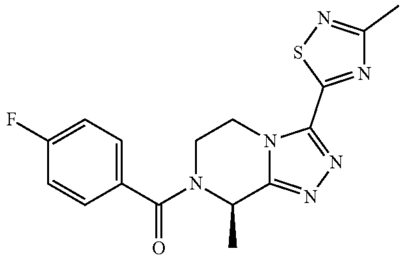

Structural formula of Fezolinetant

Fezolinetant is the first NK3 receptor antagonist used for treating VMS, which provides a therapeutic option with novel mechanism for female VMS patients, especially for the patients who are intolerant to HRT.

At present, synthesis methods of Fezolinetant mainly include the following routes.

Patent application WO2011/121137 of Ogeda discloses Route 1 as follows:

Route 1

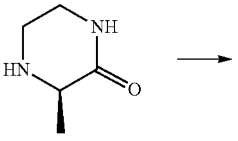

A1

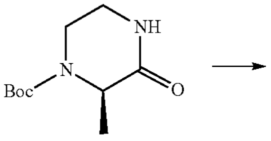

A2

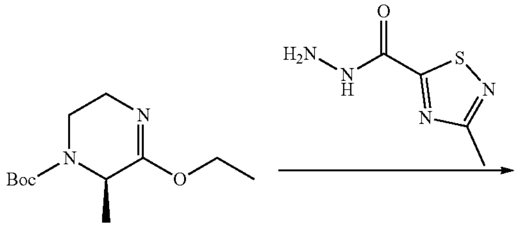

A3

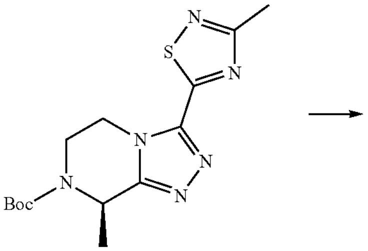

A4

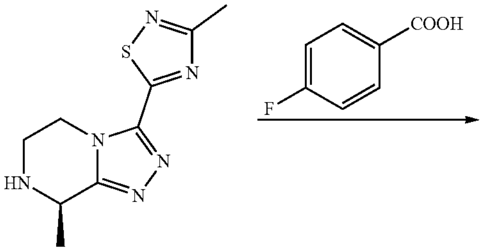

A0

-continued

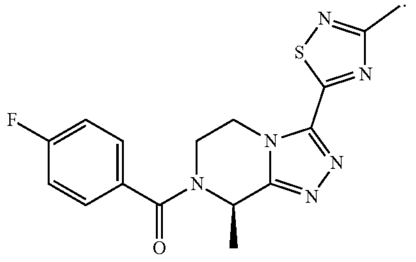

Fezolinetant

Route 1: Chiral piperazinone A1 is used as a starting material, and protected by a tert-butoxycarbonyl (Boc) amino group to obtain compound A2. Compound A2 is reacted with an ethoxylium salt in the presence of a base to obtain imine ether compound A3. Compound A3 is substituted with thiadiazole hydrazide, dehydrated and cyclized to further obtain compound A4. Under an acidic condition, the chiral key intermediate A0 is obtained by deprotection. The intermediate A0 is finally reacted with 4-fluorobenzoic acid or a derivative thereof to obtain Fezolinetant.

The chiral piperazinone A1 used in the scheme is expensive, and its overall cost is relatively high.

In addition, the route has a significant drawback, as it is prone to racemization in step 2 and step 3, making it difficult to obtain chiral compounds A4 and A0 with high chiral purity (>80% ee), which cannot be used for the preparation of active pharmaceutical ingredient of Fezolinetant.

Patent application CN103906750 B9 of Ageda makes further improvements on this route, and discloses Route 2 as follows:

Route 2

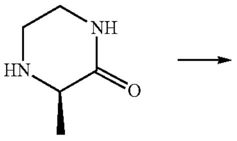

A1

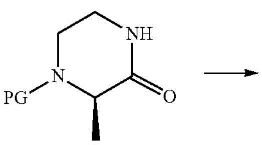

B2

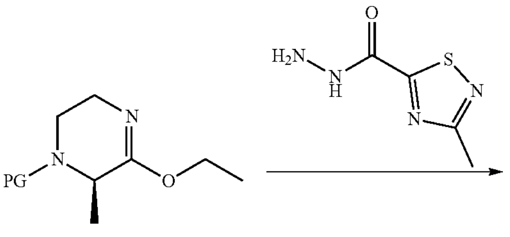

B3

-continued

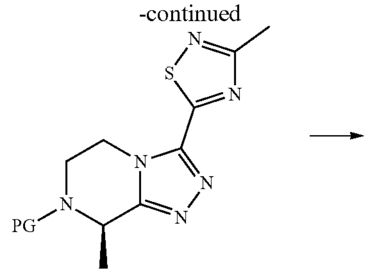

B4

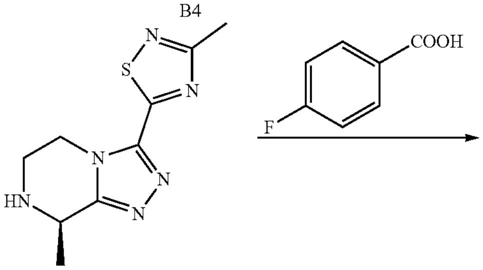

A0

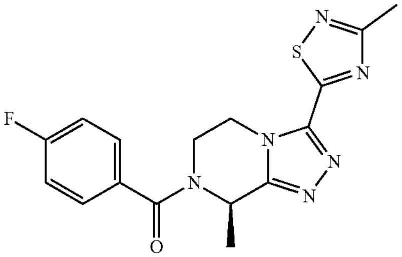

Fezolinetant

Similarly, in Route 2, chiral piperazinone A1 is used as a starting material, protected by an amino group, reacted with an ethoxylium salt, substituted with thiadiazole hydrazide, dehydrated and cyclized, deprotected, and condensed with 4-fluorobenzoic acid or a derivative thereof to obtain Fezolinetant.

Compared to Route 1, the major difference of Route 2 is that the Boc protective group has been replaced with the N-$sp^3$ protective group. Perhaps due to weakened electron withdrawing effect, the risk of occurrence of racemization of chiral center is reduced, and the chiral purity is improved.

Due to use of chiral piperazinone as an expensive material in this route, as well as the high price of the ethoxylium salt and a low yield of the second step, the overall production cost is relatively high. In addition, since the product of the second step is a high boiling point liquid, it is relatively difficult to purify.

In a further research, Ogeda invented Route 3 as follows:

Route 3

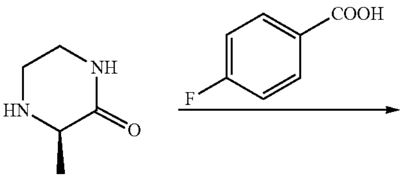

A1

-continued

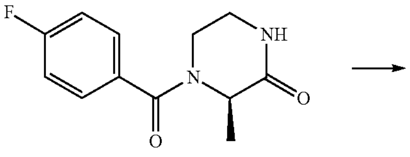

C2

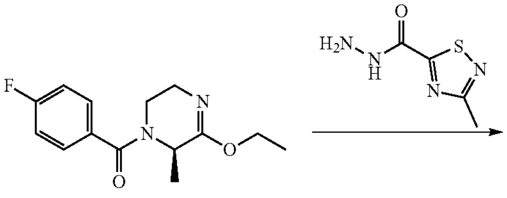

C3

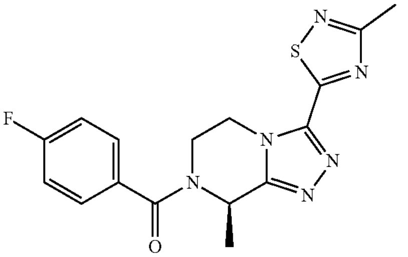

Fezolinetant

The route still starts with the same chiral piperazinone, which is reacted with 4-fluorobenzoic acid for condensation reaction, the product of which is then reacted with ethoxylium salt to obtain imine ether compound C3, which is finally reacted with thiadiazole hydrazide to obtain Fezolinetant as an active ingredient.

Obviously, compared to the first two routes, this route has an advantage of being shorter. However, due to use of N-$sp^2$ protective group, the chiral purity of the final product has been reduced. In addition, the reported yields of the last two steps of the route are less than 50%, and the overall unit material consumption is relatively high, with significant potential for improvement.

In 2023, Beijing Kanglisheng Pharmaceutical Technology Development Co., Ltd., China disclosed the following Route 4 in patent CN117510506A. The key technology lies in the final step, which uses a metal-catalyzed scheme for Suzuki coupling of the triazole ring and the thiadiazole ring.

Route 4

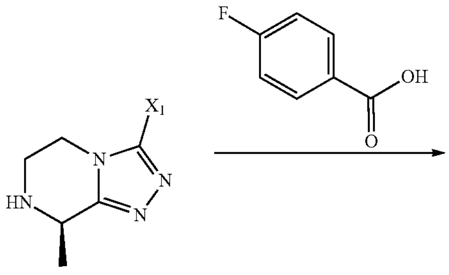

D1

-continued

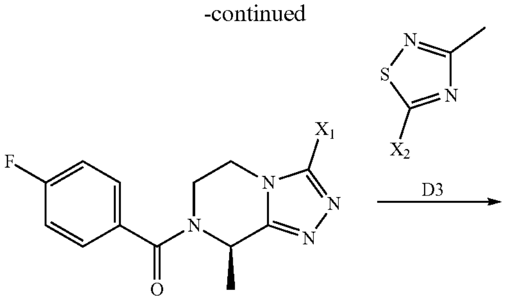

D2

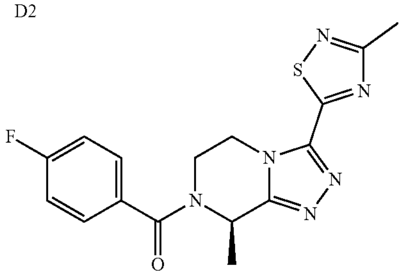

Fezolinetant

The route is shorter than any of the publicly disclosed routes and appears to have a significant cost advantage. However, in practical use, obtaining chiral raw material D1 will be a great challenge, and it will also pose a supply risk for industrialization. In addition, the use of precious metal for coupling in the final step may result in excess amount of precious metal in the active pharmaceutical ingredient, posing a significant quality risk for an oral formulation with a large dosage and long-term medication requirement.

In summary, there is still significant potential for improvement in the prior art for synthesizing Fezolinetant. Based on this, the present disclosure provides a novel route for synthesizing Fezolinetant.

SUMMARY

Aiming at solving the above problems, the present disclosure provides a method for preparing a key intermediate of Fezolinetant. Starting materials of the method are readily available, chemical reaction conditions of each step are mild, and chiral purity of each intermediate is high, which is conducive to improving chiral purity of the product, facilitating large-scale production, and reducing costs.

To achieve the above objectives, the present disclosure proposes a technical solution as follows.

In an aspect, the present disclosure provides a compound of Formula G having a following structure:

Formula G

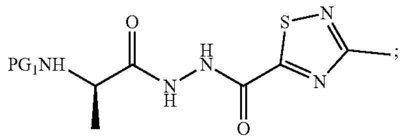

wherein $PG_1$ is a protective group.

Preferably, the $PG_1$ is tert-butoxycarbonyl, benzyloxycarbonyl or trifluoroacetyl; and more preferably, $PG_1$ is tert-butoxycarbonyl or benzyloxycarbonyl.

In another aspect, the present disclosure provides a method for preparing the compound of Formula G, comprising:

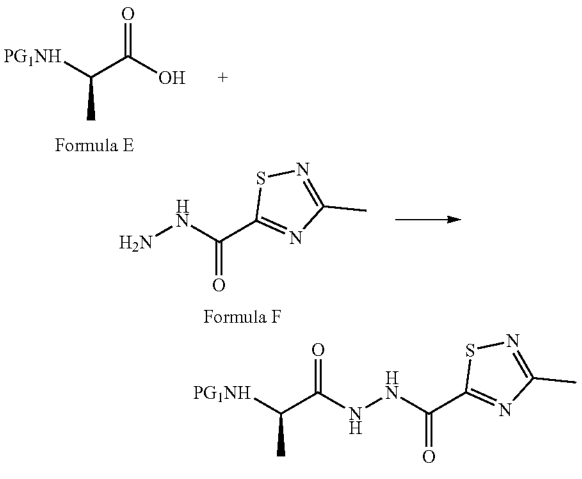

Formula E

Formula F

Formula G reacting chiral alanine of Formula E with thiadiazole hydrazide of Formula F for a condensation reaction to obtain a dihydrazide compound of Formula G;

wherein $PG_1$ is a protective group.

Preferably, the $PG_1$ is tert-butoxycarbonyl, benzyloxycarbonyl or trifluoroacetyl; and more preferably, the $PG_1$ is tert-butoxycarbonyl or benzyloxycarbonyl.

Preferably, the condensation reaction is a reaction of Formula E with Formula F in the presence of a condensing agent, or condensation of Formula E with isobutyl chloroformate in the presence of a base to form a mixed anhydride, which is then reacted with Formula F. More preferably, the condensation reaction is the condensation of Formula E with isobutyl chloroformate in the presence of a base to form a mixed anhydride, which is then reacted with Formula F.

Preferably, the base is at least one selected from the group consisting of N-methylmorpholine and N,N-diisopropylethylamine; and more preferably, the base is N-methylmorpholine.

The condensing agent is at least one selected from the group consisting of dicyclohexylcarbodiimide, diisopropylcarbodiimide, 1-(3-dimethylaminopropyl)-3-ethylcarbodiimide, methyl ethylphosphinic anhydride, diphenylphosphinyl chloride, and 2-(7-azabenzotriazole)-N,N,N',N'-tetramethylurea hexafluorophosphate; and more preferably, the condensing agent is at least one selected from the group consisting of 1-(3-dimethylaminopropyl)-3-ethylcarbodiimide, and 2-(7-azabenzotriazole)-N,N,N',N'-tetramethylurea hexafluorophosphate.

Preferably, the condensation reaction further comprises a solvent.

Preferably, the solvent is at least one selected from the group consisting of tetrahydrofuran, dioxane, ethyl acetate, isopropyl acetate and dichloromethane; and more preferably, the solvent is ethyl acetate.

In an aspect, the present disclosure provides a compound of Formula H having a following structure:

Formula H

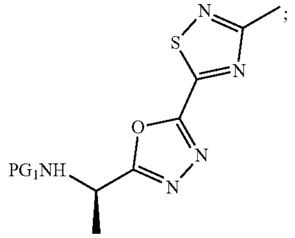

;

wherein $PG_1$ is a protective group.

Preferably, the $PG_1$ is tert-butoxycarbonyl, benzyloxycarbonyl or trifluoroacetyl; and more preferably, the $PG_1$ is tert-butoxycarbonyl or benzyloxycarbonyl.

In another aspect, the present disclosure provides a method for preparing the compound of Formula H, comprising:

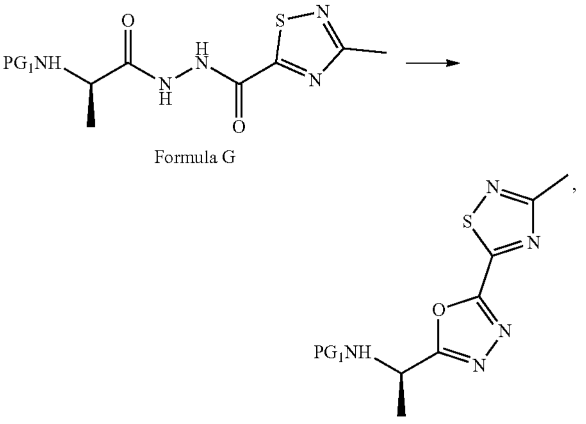

Formula G

,

Formula H subjecting a dihydrazide compound of Formula G to a reaction in the presence of a condensing agent, dehydrating, and cyclizing to obtain the compound of Formula H;

wherein $PG_1$ is a protective group.

Preferably, the $PG_1$ is tert-butoxycarbonyl, benzyloxycarbonyl or trifluoroacetyl; and more preferably, $PG_1$ is tert-butoxycarbonyl or benzyloxycarbonyl.

Preferably, the condensing agent is at least one selected from the group consisting of a combination reagent of iodine and triphenylphosphine, and Burgess reagent; and more preferably, the condensing agent is Burgess reagent.

Preferably, the Burgess reagent has a structure as follows:

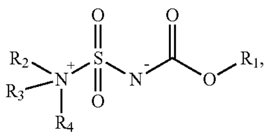

, wherein $R_1$, $R_2$, $R_3$, and $R_4$ are each independently alkyl groups.

Preferably, the reaction further comprises a solvent.

Preferably, the solvent is at least one selected from the group consisting of tetrahydrofuran, dioxane, ethyl acetate, isopropyl acetate and dichloromethane; and more preferably, the solvent is dichloromethane.

In an aspect, the present disclosure provides a compound of Formula I having a following structure:

Formula I

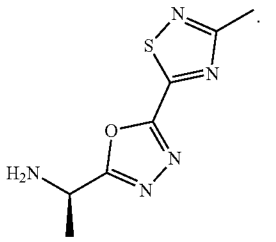

In another aspect, the present disclosure provides a method for preparing the compound of Formula I, comprising:

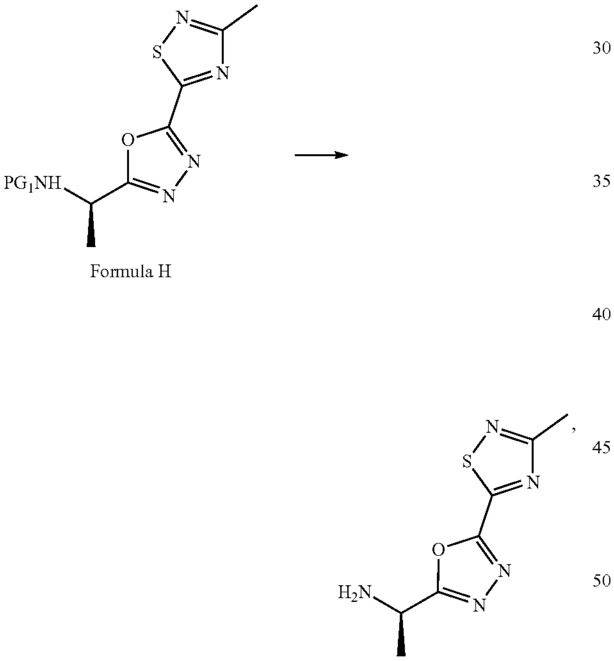

Formula H

Formula I deprotecting a compound of Formula H to obtain the compound of Formula I or a salt thereof;

wherein $PG_1$ is a protective group.

Preferably, the $PG_1$ is tert-butoxycarbonyl, benzyloxycarbonyl or trifluoroacetyl; and more preferably, $PG_1$ is tert-butoxycarbonyl or benzyloxycarbonyl.

Preferably, the salt is a hydrochloride salt, a hydrogen bromide salt, a p-toluenesulfonic acid salt, or a methylsulfonic acid salt.

In an aspect, the present disclosure provides a compound of Formula J having a following structure:

Formula J

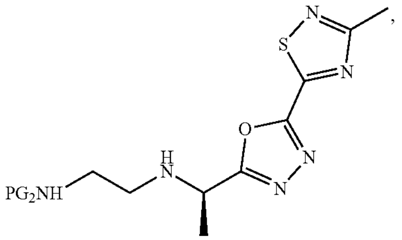

wherein $PG_2$ is a protective group.

Preferably, $PG_2$ is tert-butoxycarbonyl or benzyloxycarbonyl.

In another aspect, the present disclosure provides a method for preparing the compound of Formula J, comprising:

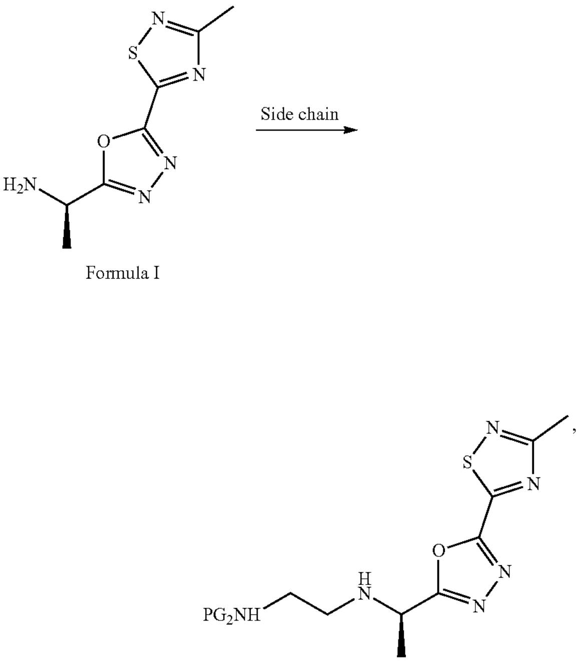

Formula I

Formula J reacting a compound of Formula I with a side chain for a substitution reaction to obtain the compound of Formula J;

wherein $PG_2$ is a protective group.

Preferably, the $PG_2$ is tert-butoxycarbonyl or benzyloxycarbonyl.

Preferably, the side chain is at least one selected from the group consisting of 2-$PG_2$ aminoacetaldehyde, 2-$PG_2$ aminoethyl bromide, 2-$PG_2$ amino-1-p-toluenesulfonyloxyethane, 2-$PG_2$ amino-1-methylsulfonyloxyethane, and 1,2,3-oxathiazolidine-3-$PG_2$-2,2-dioxide;

The side chain has a structure as follows:

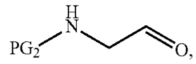, 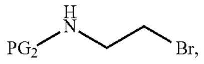,

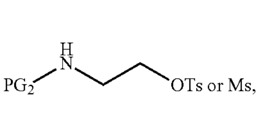, or 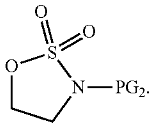.

In another aspect, the present disclosure provides use of the compound of Formula G as described above in the synthesis of a key intermediate A0 of Fezolinetant.

The present disclosure provides use of the compound of Formula H as described above in the synthesis of a key intermediate A0 of Fezolinetant.

The present disclosure provides use of the compound of Formula I as described above in the synthesis of a key intermediate A0 of Fezolinetant.

The present disclosure provides use of the compound of Formula J as described above in the synthesis of a key intermediate A0 of Fezolinetant.

In another aspect, the present disclosure provides a method for preparing a key intermediate A0 of Fezolinetant, comprising: subjecting the compound of Formula G, the compound of Formula H, the compound of Formula I, and the compound of Formula J as mentioned above to reactions of a synthesis route as follows:

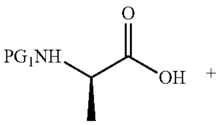

Formula E

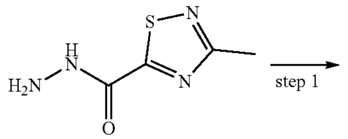

Formula F

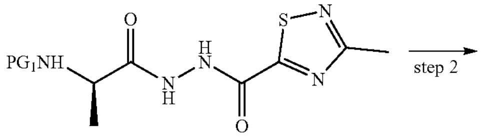

Formula G

-continued

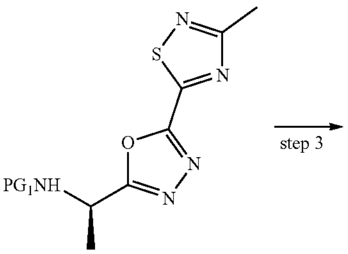

Formula H

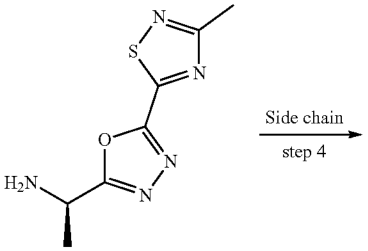

Formula I

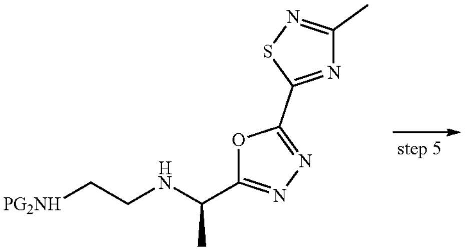

Formula J

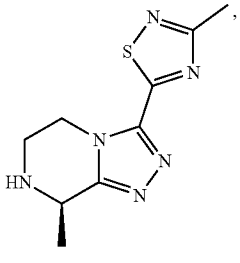,

A0 wherein $PG_1$ and $PG_2$ are protective groups.

Preferably, the $PG_1$ is tert-butoxycarbonyl, benzyloxycarbonyl or trifluoroacetyl; and the $PG_2$ is tert-butoxycarbonyl or benzyloxycarbonyl. More preferably, the $PG_1$ is tert-butoxycarbonyl or benzyloxycarbonyl; and the $PG_2$ is tert-butoxycarbonyl or benzyloxycarbonyl.

Preferably, a specific reaction process of step 5 is as follows: the compound of Formula J is deprotected to obtain a diamine structure Ja; the diamine structure Ja undergoes a molecular reaction to obtain compound Jb, since it is extremely unstable in an alkaline state; and finally, the compound Jb undergoes a heating condition to obtain compound A0.

The route of reaction mechanism of step 5 is as follows:

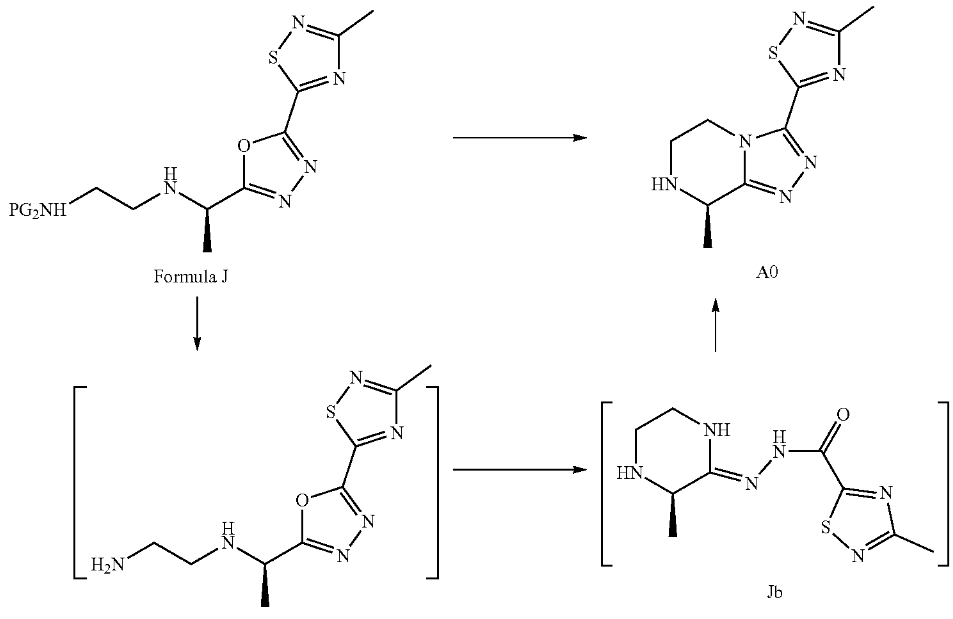

Formula J, A0, Ja, Jb

Compared to the prior art, the present disclosure has the following beneficial effects:

1. The present disclosure provides a novel route for synthesizing a key intermediate A0 of Fezolinetant, which provides new ideas and possibilities for the synthesis of key intermediate A0 of Fezolinetant.

2. Starting materials of the novel route provided by the present disclosure are readily available, chemical reaction conditions of each step are mild, and chiral purity of each intermediate is high, which is conducive to improving chiral purity of the product.

3. The present disclosure also provides four new compounds, namely a compound of Formula G, a compound of Formula H, a compound of Formula I, and a compound of Formula J.

DETAILED DESCRIPTION

Figure 1:
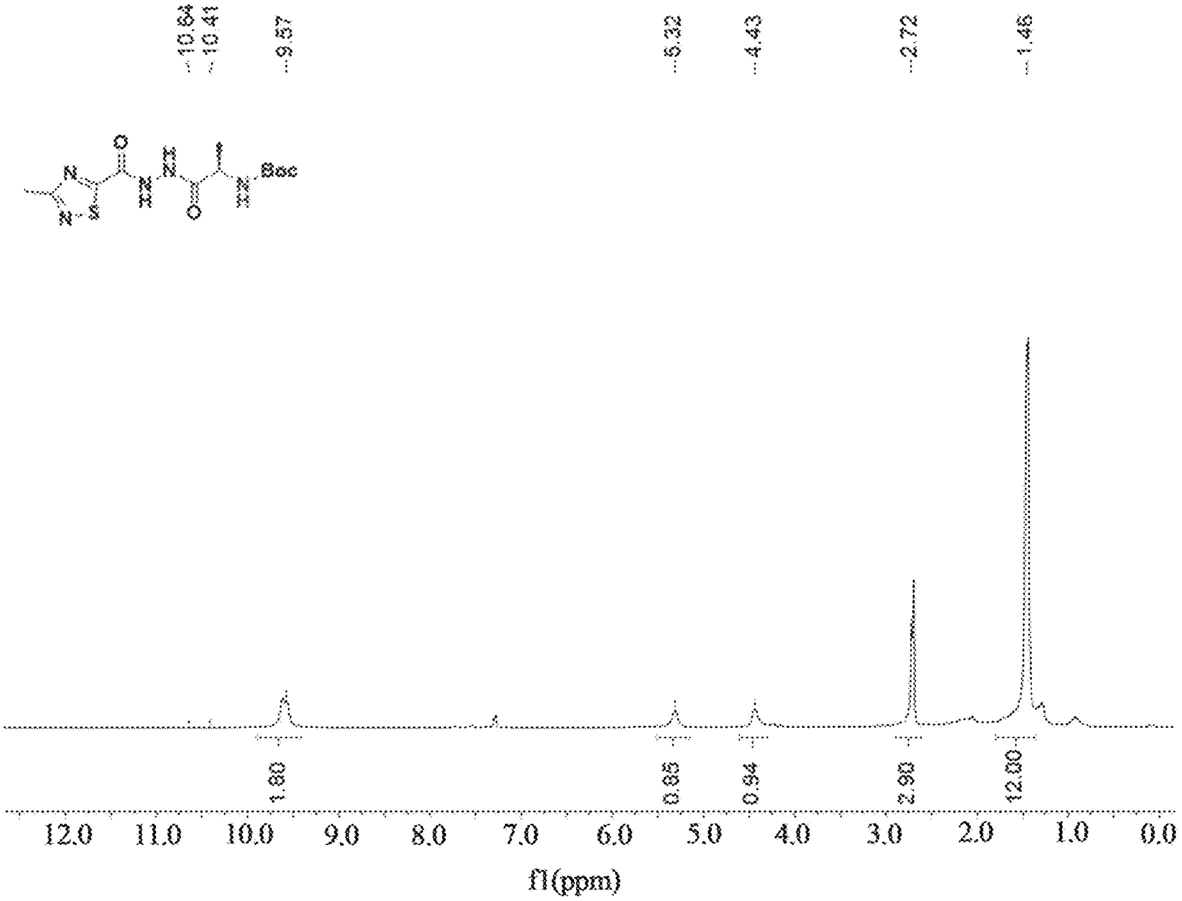
FIG. 1 shows a $^1$HNMR spectrum of compound G1.
Figure 2:
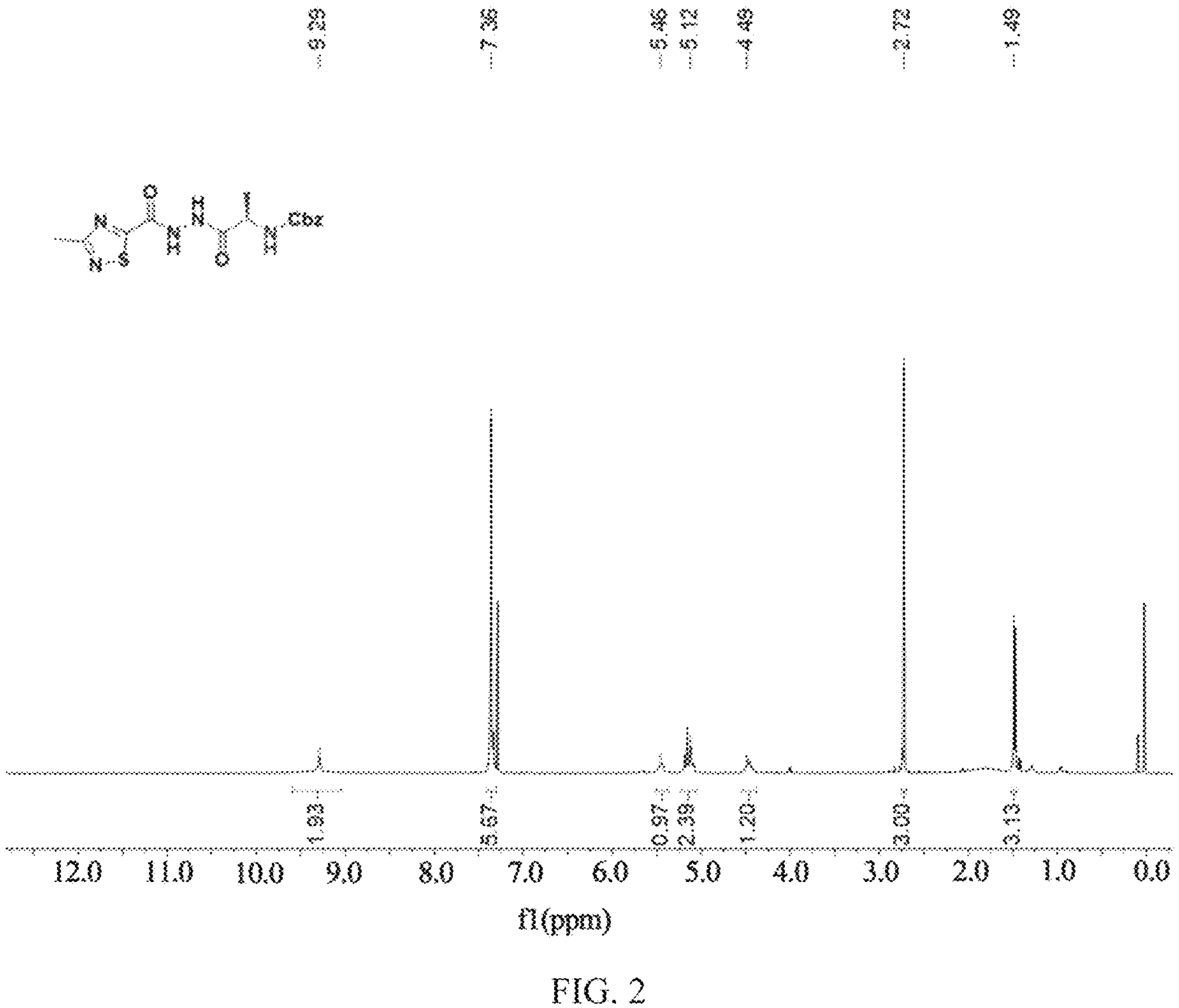
FIG. 2 shows a $^1$HNMR spectrum of compound G2.
Figure 3:
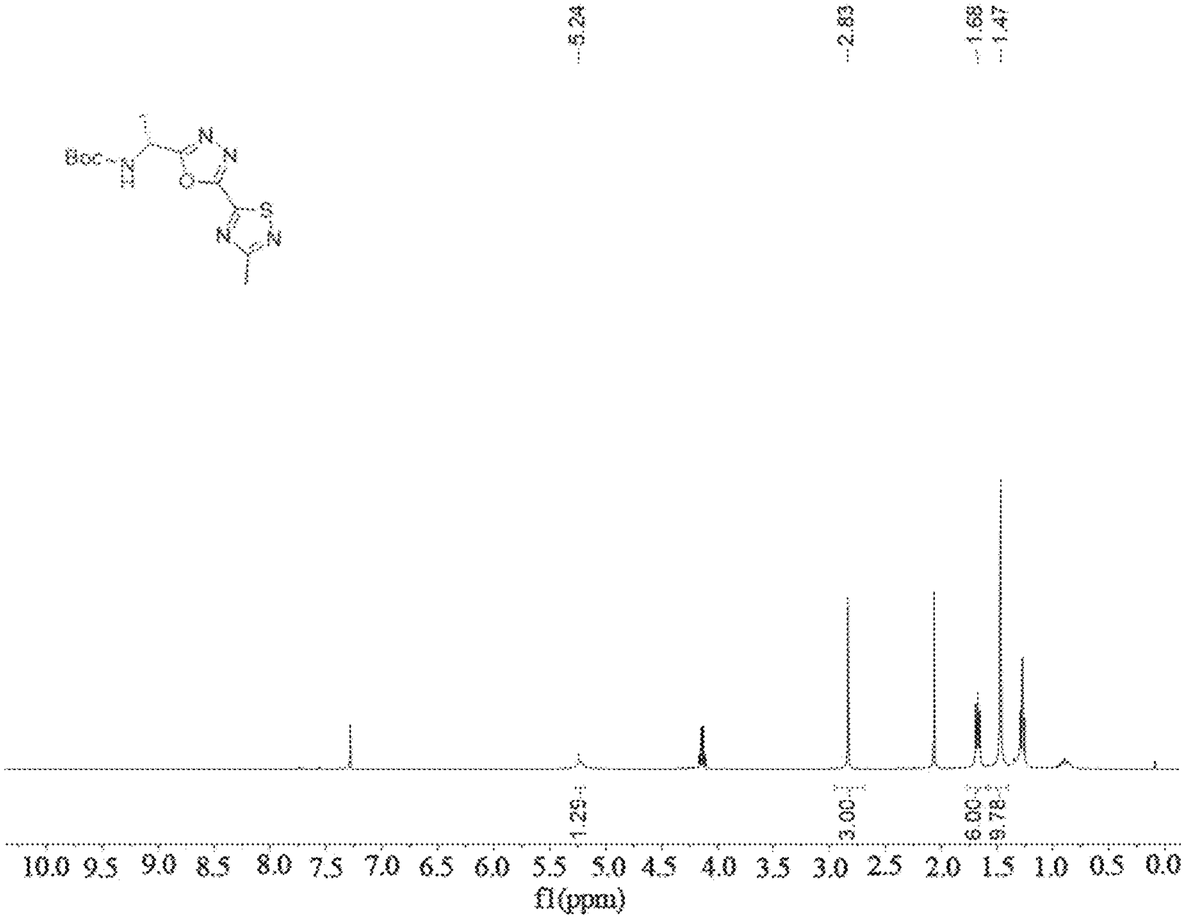
FIG. 3 shows a $^1$HNMR spectrum of compound H1.
Figure 4:
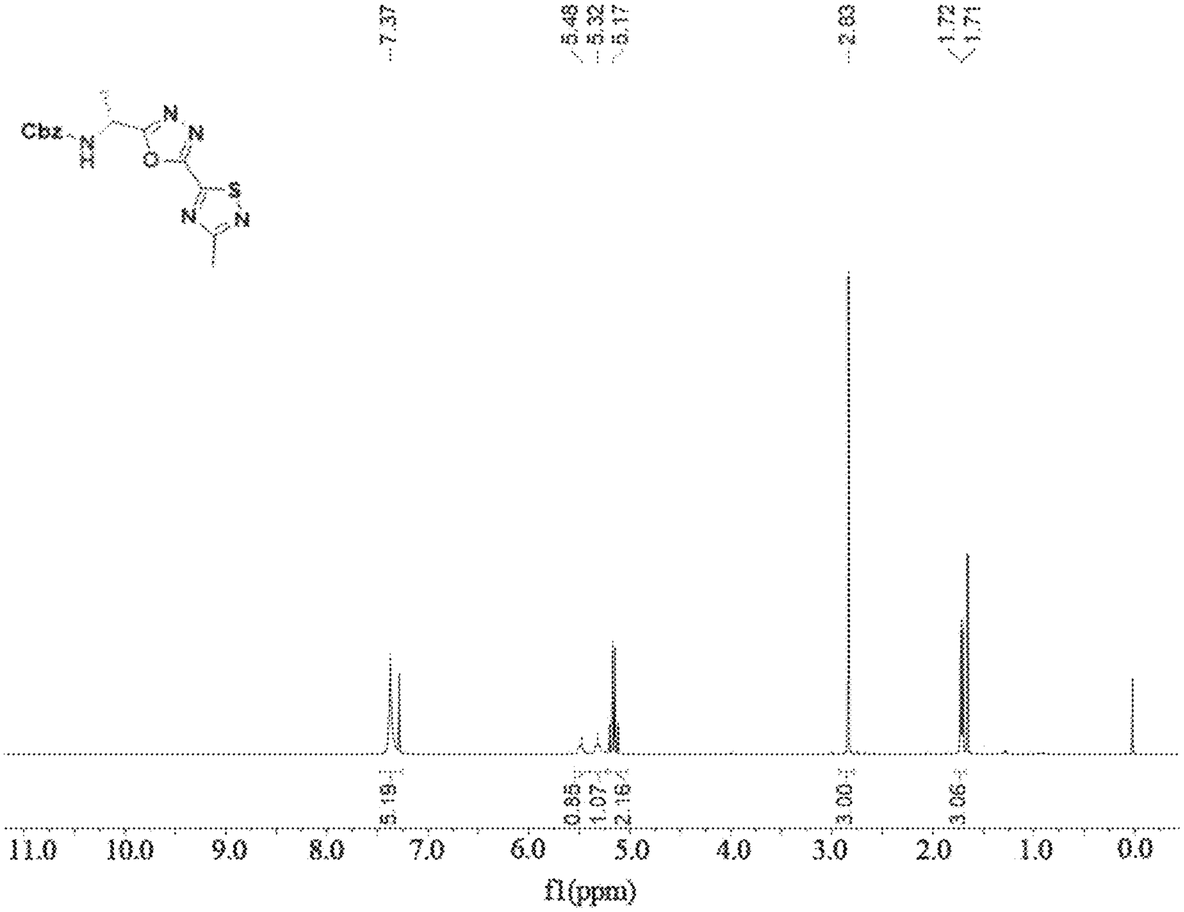
FIG. 4 shows a $^1$HNMR spectrum of compound H2.
Figure 5:
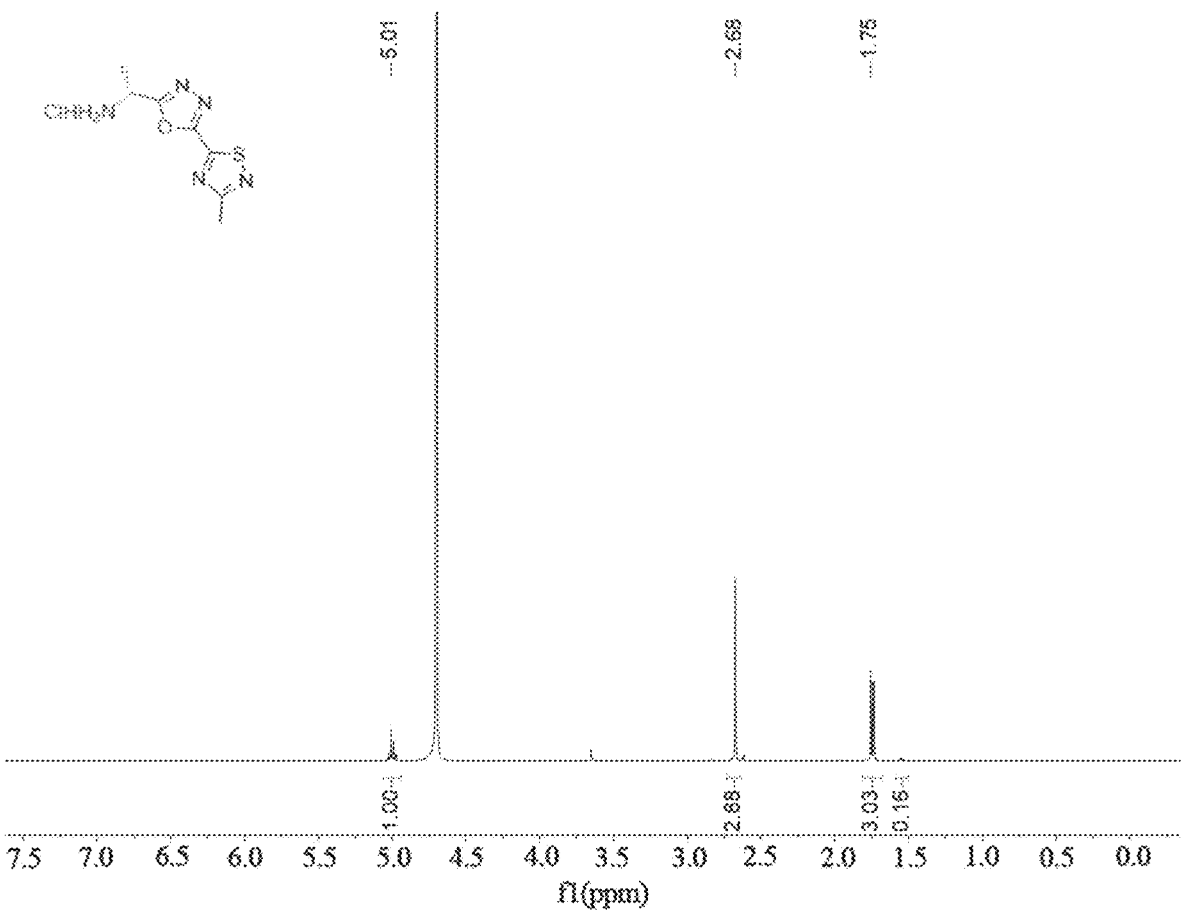
FIG. 5 shows a $^1$HNMR spectrum of compound I1.
Figure 6:
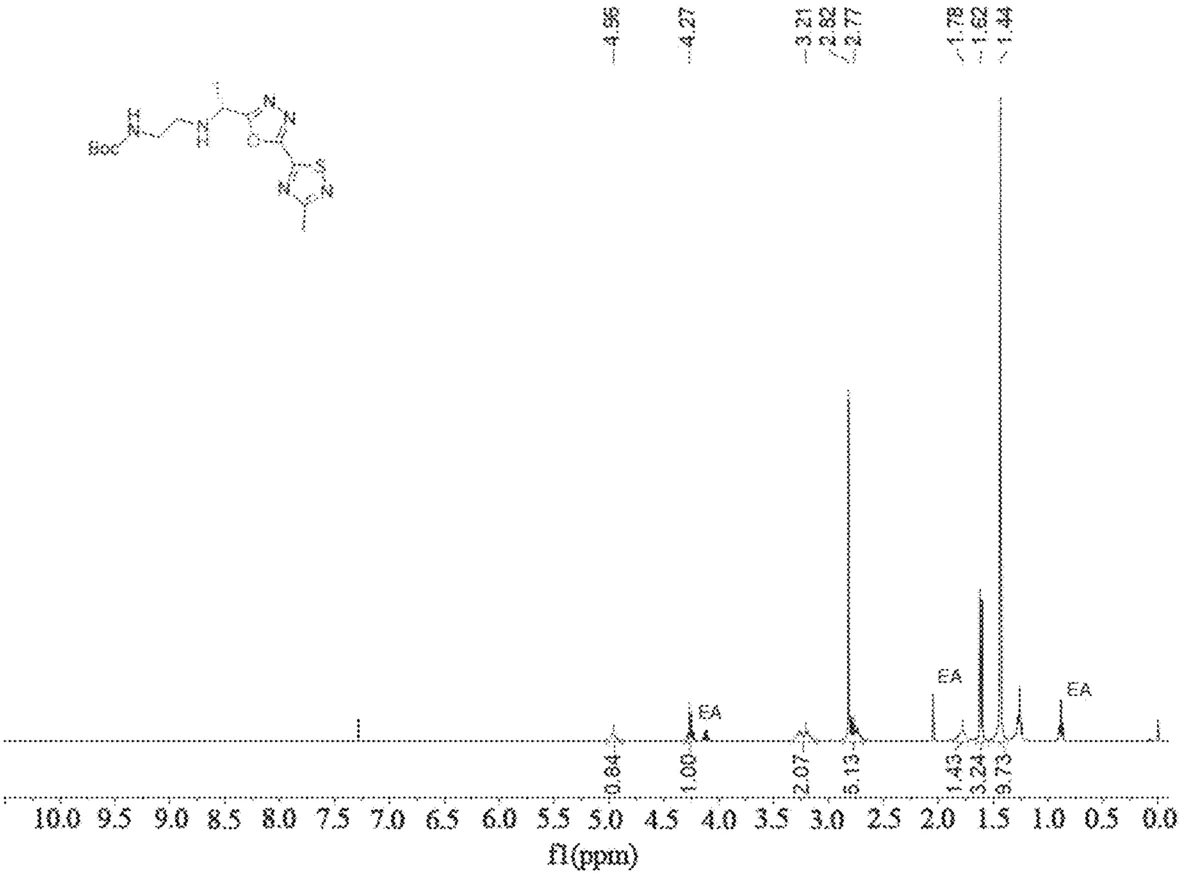
FIG. 6 shows a $^1$HNMR spectrum of compound J1.
Figure 7:
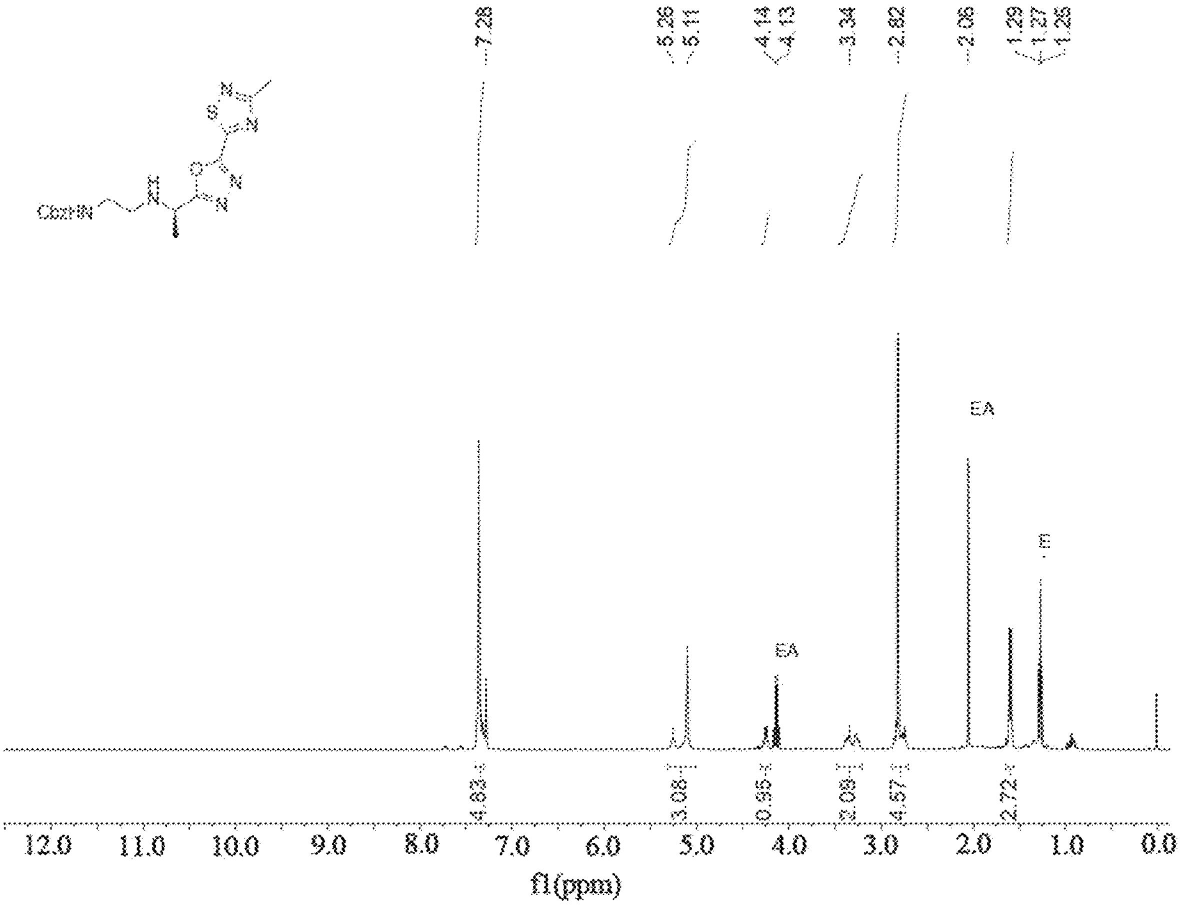
FIG. 7 shows a $^1$HNMR spectrum of compound J2.
Figure 8:
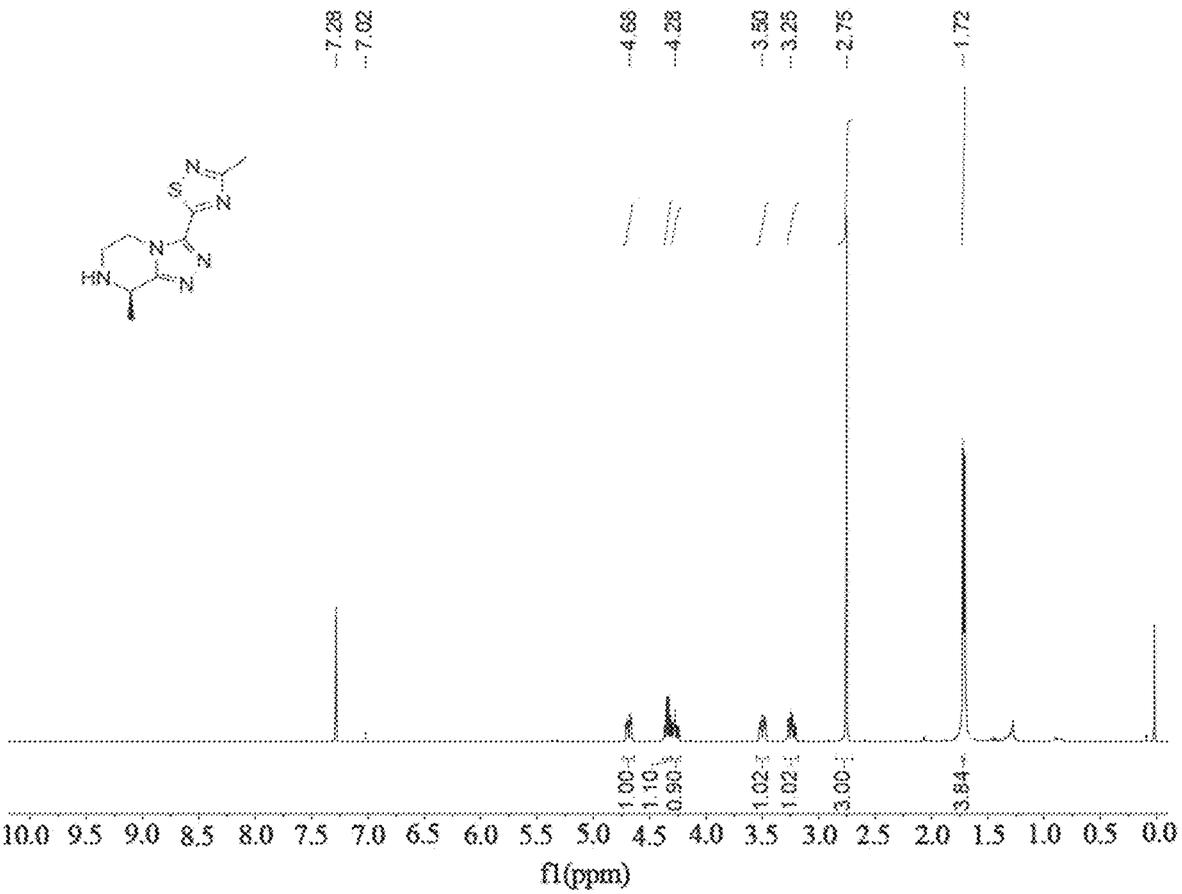
FIG. 8 shows a $^1$HNMR spectrum of compound A0.
Figure 9:
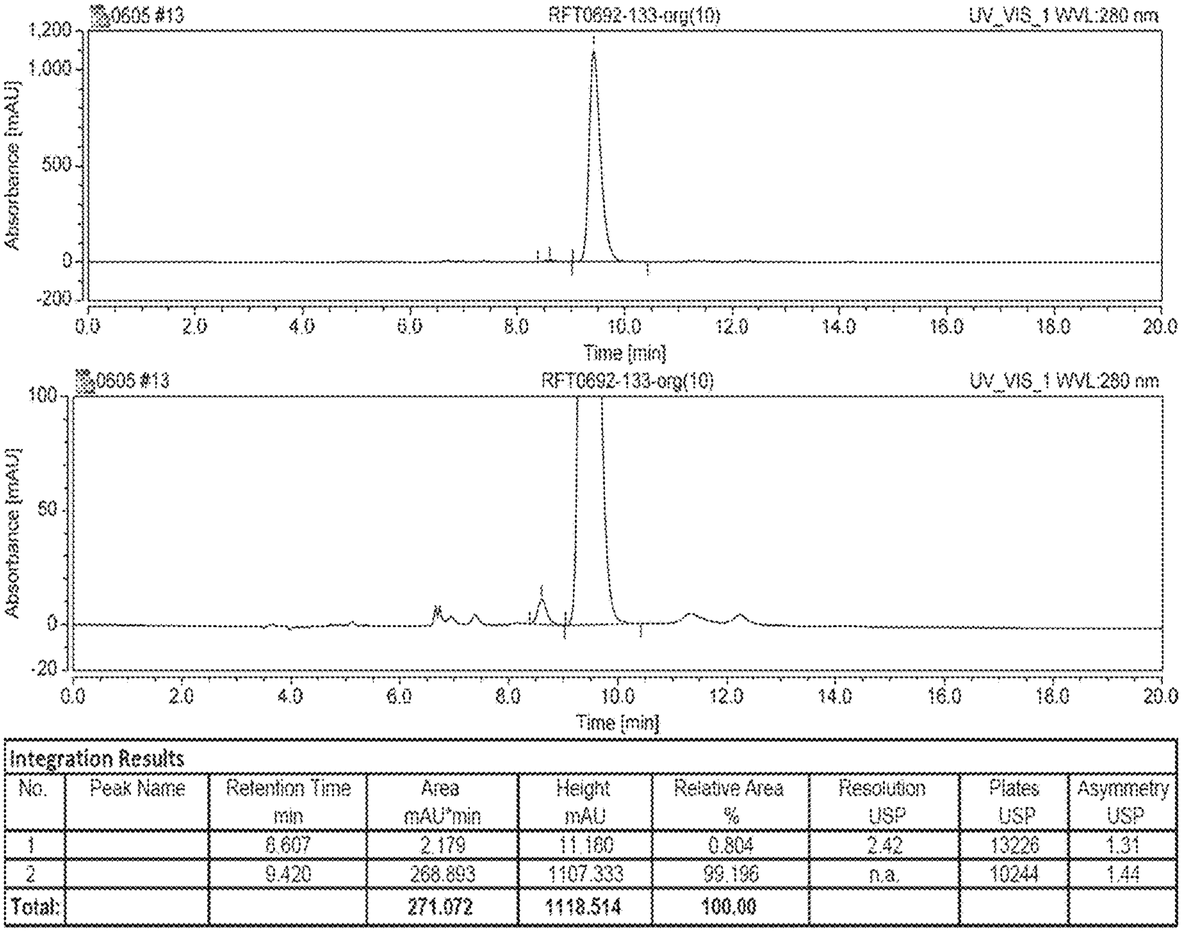
FIG. 9 shows a chiral purity spectrum of compound A0.
Figure 10:
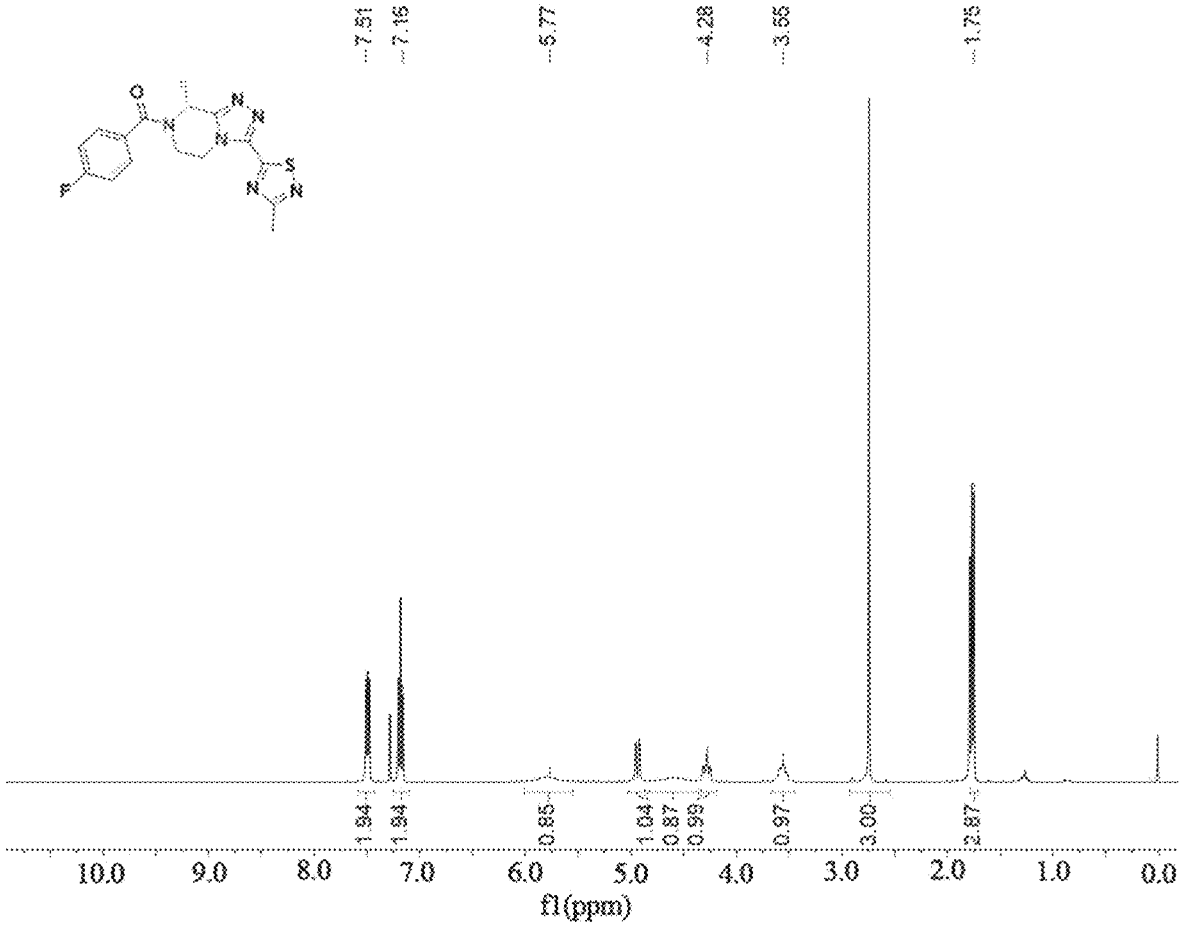
FIG. 10 shows a $^1$HNMR spectrum of Fezolinetant.
Figure 11:
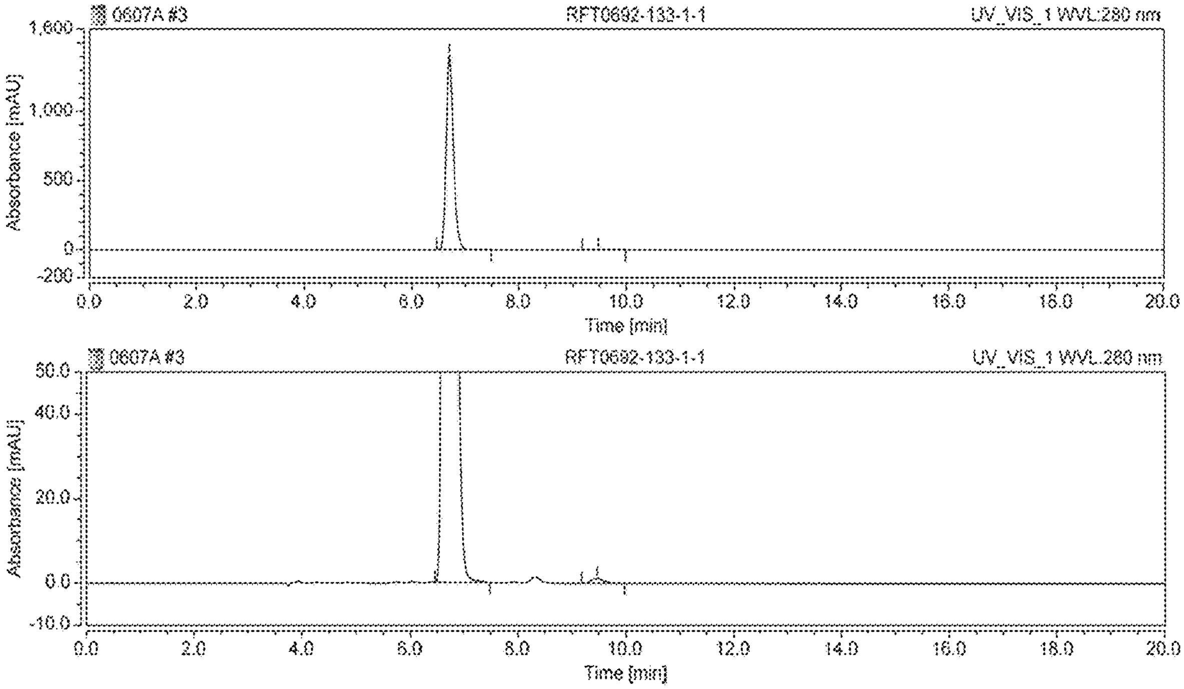
FIG. 11 shows a chiral purity spectrum of Fezolinetant.

In order to make the technical means, inventive features, purposes and effects realized by the present disclosure easy to understand, the following specific examples are combined to further illustrate the present disclosure. However, the following examples are only preferred examples of the present disclosure and are not exhaustive. Based on the embodiments described in the below, any other embodiments obtained by those skilled in the art without creative labor are within the scope of protection of the present disclosure. It is worth noting that the raw materials used in the present disclosure are all ordinary commercially available products, and their sources are not specifically limited. The technical and scientific terms used in the examples have the meanings that are commonly understood by those ordinary skilled in the art to which the present disclosure belongs.

Definition

Boc: tert-butoxycarbonyl;
Cbz: benzyloxycarbonyl;
PMB: p-methoxybenzyl;
DCC: dicyclohexylcarbodiimide
DIC: diisopropylcarbodiimide
EDCI: 1-(3-dimethylaminopropyl)-3-ethylcarbodiimide
HATU: 2-(7-azabenzotriazole)-N,N,N',N'-tetramethylurea hexafluorophosphate
CDI: carbonyl diimidazole

Example 1

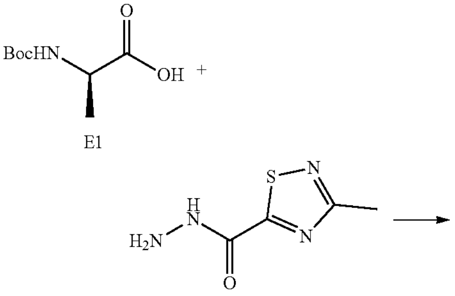

E1 + F

-continued

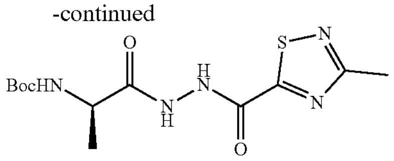

G1

Compound E1 (54.0 g, 1.0 eq.), N-methylmorpholine (34.6 g, 1.2 eq.) and 540 mL of tetrahydrofuran were added to a 100 mL three-necked flask, and cooled to a temperature of 0° C. under nitrogen protection. Temperature inside the reaction flask was controlled to between −10° C. and 10° C., and isobutyl chloroformate (40.9 g, 1.05 eq.) was added dropwise. After dropwise addition, a resulting mixture was stirred for 20 minutes at a holding temperature, and compound F (45.1 g, 1.0 eq.) was added in batches. After adding the compound F, a resulting mixture was stirred for 10 minutes at a holding temperature. 10% aqueous citric acid solution was added. Tetrahydrofuran was removed by concentration under reduced pressure, dichloromethane was added for extraction for twice, and the obtained organic phase was concentrated to obtain a crude product. The crude product was subjected to silica gel column chromatography to obtain 76.1 g of compound G1, with a yield of 81% as light yellow solid. The chiral purity was 99.9%.

LCMS, [M+Na]=352;

$^1$HNMR ($CDCl_3$) δ9.63 (br, 2H), 5.32 (br, 1H), 4.43 (br, 1H), 2.70 (s, 3H), 1.46 (br, 12H). Interconversion of ketene configurations was present in the nuclear magnetic resonance (NMR) spectrum.

Example 2

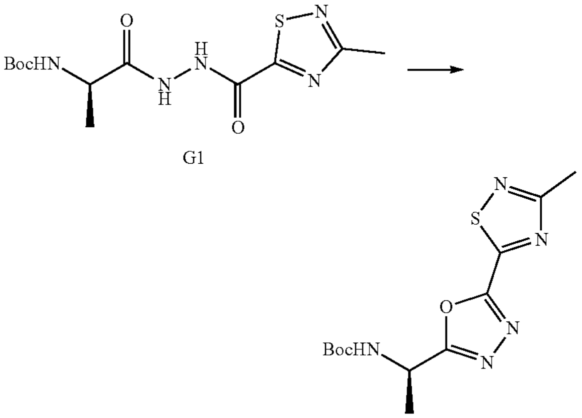

G1

H1

380 mL of tetrahydrofuran and chlorosulfonic acid isocyanate (48.9 g, 3.0 eq.) were added to a 500 mL three-necked flask, and cooled to a temperature of 0-10° C. under nitrogen protection. Methanol (11.1 g, 3.0 eq.) was added dropwise at a holding temperature, and stirred for 10 minutes to obtain a solution A.

Compound G1 (38.0 g, 1.0 eq.), triethylamine (75.8 g, 6.5 eq.), and 380 mL of tetrahydrofuran were added to a 1000 mL three-necked reaction flask, and cooled to a temperature of 0-10° C. under nitrogen protection to obtain a solution B. The solution A was added dropwise to the solution B, and a resulting mixture was heated to 20-40° C. to react for 30 hours. A reacted solvent was concentrated, and a resulting concentrate was diluted with 500 mL of dichloromethane, then washed with a 5% sodium bicarbonate solution, and dried with saturated sodium chloride. The organic phase was concentrated to dryness, was and then purified by silica gel column chromatography to obtain 30.5 g of compound H1, with a yield of 85% as white solid. The chiral purity was 99.9%.

LCMS, [M+H]=312;

$^1$HNMR ($CDCl_3$) δ5.25 (br, 1H), 2.82 (s, 3H), 2.72 (s, 1H), 1.70 (d, 3H), 1.46 (s, 9H).

Example 3

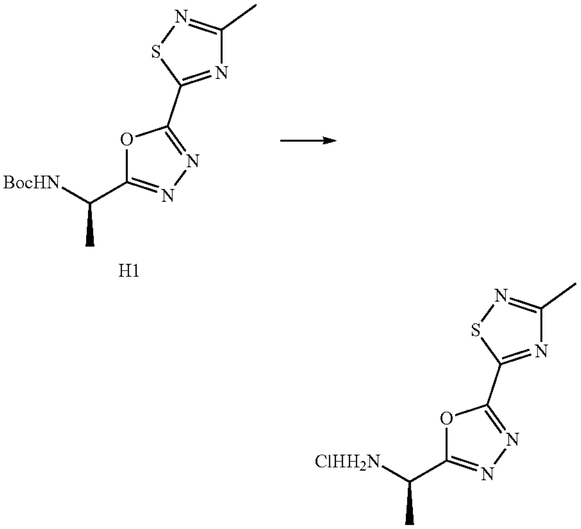

H1

I1

Compound H1 (12.0 g, 1.0 eq.) and 60 mL of dioxane were added to a 250 mL three-necked flask, and stirred until a resulting solution became clear; and then a solution of hydrogen chloride in dioxane (4 M, 60 mL) were added dropwise at 20-30° C. After dropwise addition, a resulting mixture was stirred for 2 hours at room temperature, filtered, and dried to obtain 9.1 g of compound I1, with a yield of 95% as white solid. The chiral purity was 99.9%.

LCMS: [M+1]=212;

$^1$HNMR ($D_2O$) δ5.01 (q, 1H), 2.88 (s, 3H), 1.75 (d, 3H).

Example 4

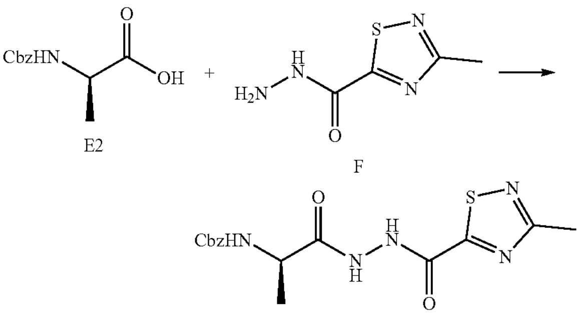

E2

F

G2

Compound E2 (5 g, 1.0 eq.), N-methylmorpholine (2.7 g, 1.2 eq.), and 50 mL of tetrahydrofuran were added to a 100 mL three-necked flask, and cooled to a temperature of 0° C. under nitrogen protection. Temperature inside the reaction flask was controlled to between −10° C. and 10° C., and isobutyl chloroformate (3.2 g, 1.05 eq.) was added dropwise. After dropwise addition, a resulting mixture was stirred for 20 minutes at a holding temperature, and compound F (3.5 g, 1.0 eq.) was added in batches. After adding the compound F, a resulting mixture was stirred for 10 minutes at a holding temperature. 10% aqueous citric acid solution was added. Tetrahydrofuran was removed by concentration under reduced pressure, dichloromethane was added for extraction for twice, and the obtained organic phase was concentrated to obtain a crude product. The crude product was subjected to silica gel column chromatography to obtain 6.7 g of compound G2, with a yield of 82% as light yellow oil. The chiral purity was 99.9%.

LCMS, [M+1]=364;

$^1$HNMR ($CDCl_3$) δ9.29 (br, 2H), 7.36 (m, 5H), 5.45 (br, 1H), 5.16 (m, 2H), 4.48 (m, 1H), 2.72 (s, 3H), 1.49 (d, 3H).

Example 5

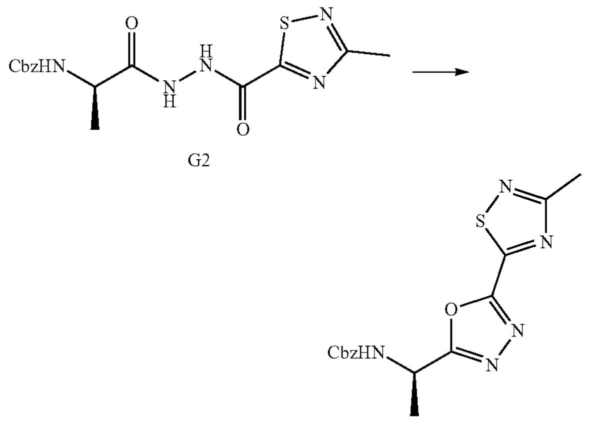

G2

H2

50 mL of tetrahydrofuran and chlorosulfonic acid isocyanate (5.8 g, 3.0 eq.) were added to a 100 mL three-necked flask, and cooled to a temperature of 0-10° C. under nitrogen protection. Methanol (1.32 g, 3.0 eq.) was added dropwise at a holding temperature, and stirred for 10 minutes to obtain a solution A.

Compound G2 (5.0 g, 1.0 eq.), triethylamine (9.0 g, 6.5 eq.), and 50 mL of tetrahydrofuran were added to a 250 mL three-necked reaction flask, and cooled to a temperature of 0-10° C. under nitrogen protection to obtain a solution B. The solution A was added dropwise to the solution B, and a resulting mixture was heated to 20-40° C. to react for 24 hours. A reacted solvent was concentrated, and a resulting concentrate was diluted with 100 mL of dichloromethane, then washed with a 5% sodium bicarbonate solution, and dried with saturated sodium chloride. The organic phase was concentrated to dryness, and then purified by silica gel column chromatography to obtain 3.94 g of compound H2, with a yield of 83% as light yellow liquid. The chiral purity was 99.9%.

LCMS: [M+1]=346;

$^1$HNMR ($CDCl_3$) δ7.37 (m, 5H), 5.48 (br, 1H), 5.32 (m, 1H), 5.17 (m, 2H), 2.83 (s, 3H), 1.72 (d, 3H).

Example 6

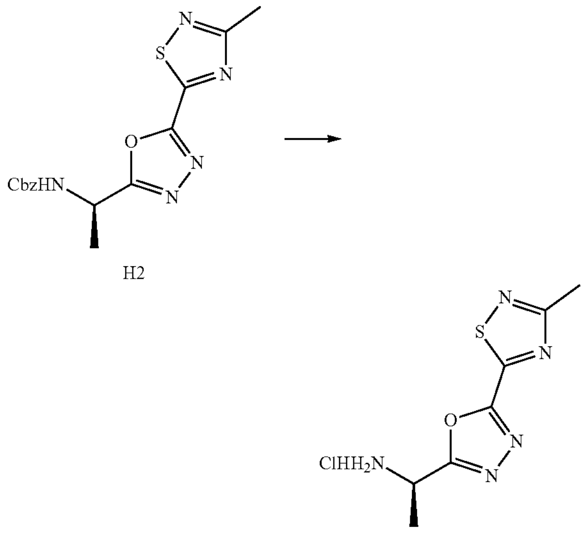

H2

I1

Compound H2 (1 g, 1.0 eq.), 30 mL of methanol, 2 mL of a solution of hydrogen chloride in methanol (4 M), and 0.3 g of 10% palladium on carbon were added to a 100 mL single neck flask. The flask was vacuumized, purged with nitrogen for three times, and then stirred overnight at room temperature under a hydrogen atmosphere. The palladium on carbon was filtered and washed with methanol. Filtrate was concentrated to dryness to obtain a crude product. 20 mL of ethyl acetate was added to the crude product, a resulting mixture was slurried at room temperature for 30 minutes, filtered and dried to obtain 0.7 g of compound I1, with a yield of 98% as white solid. The chiral purity was 99.9%.

Example 7

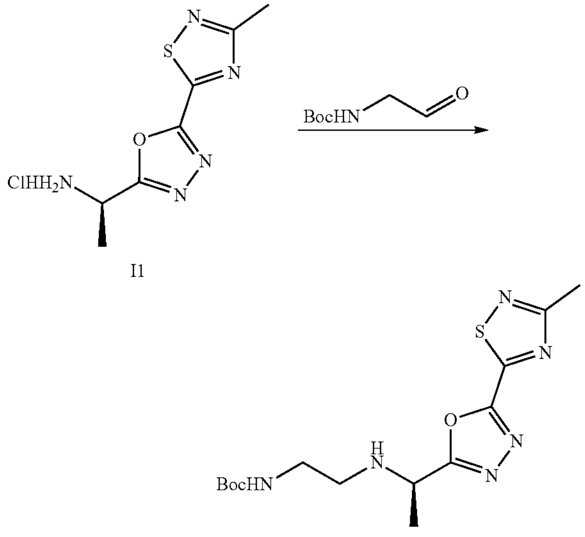

I1

J1

Compound I1 (10 g, 1.0 eq.), Boc aminoacetaldehyde (7.7 g, 1.2 eq.) and 100 mL of dichloromethane was added to a 250 mL three-necked flask, and cooled to a temperature of 0-10° C. under nitrogen protection. Sodium triacetoxyborohydride (17.2 g, 2.0 eq.) was added in batches at a holding temperature. After dropwise addition, a resulting mixture was stirred for 2 hours at room temperature. A reacted solution was washed with a 5% sodium bicarbonate solution and a saturated saline solution, respectively. The organic phase was concentrated to dryness to obtain a crude product, and the crude product was purified by silica gel column chromatography to obtain 12.2 g of compound J2, with a yield of 85% as white solid. The chiral purity was 99.9%.

LCMS: [M+1]=355;

$^{1}$HNMR ($CDCl_3$) δ6.96 (br, 1H), 5.1 (s, 2H), 4.27 (q, 1H), 3.21 (m, 2H), 2.82 (s, 3H), 2.77 (m, 2H), 1.62 (d, 3H).

Example 8

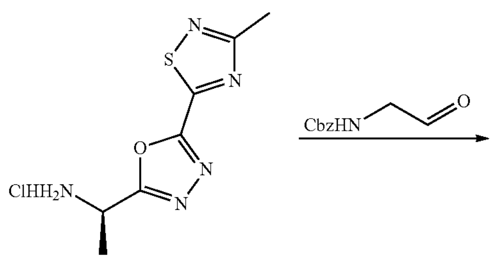

I1

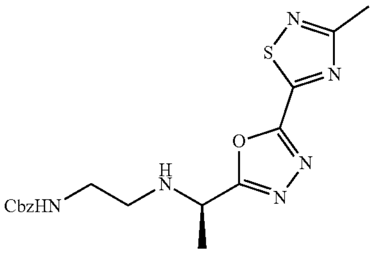

J2

Compound I1 (13.5 g, 1.0 eq.), Cbz aminoacetaldehyde (9.4 g, 1.2 eq.) and 135 mL of dichloromethane was added to a 250 mL three-necked flask, and cooled to a temperature of 0-10° C. under nitrogen protection. Sodium triacetoxyborohydride (17.2 g, 2.0 eq.) was added in batches at a holding temperature. After dropwise addition, a resulting mixture was stirred for 2 hours at room temperature. A reacted solution was washed with a 5% sodium bicarbonate solution and a saturated saline solution, respectively. The organic phase was concentrated to dryness to obtain a crude product, and the crude product was purified by silica gel column chromatography to obtain 13.5 g of compound J2, with a yield of 83% as light yellow oil. The chiral purity was 99.9%.

LCMS: [M+1]=402;

$^{1}$HNMR ($CDCl_3$) δ7.28 (m, 5H), 5.26 (brs, 1H), 5.1 (s, 2H), 4.24 (m, 1H), 3.35 (m, 2H), 2.82 (s, 3H), 2.77 (m, 2H), 1.60 (d, 3H).

Example 9

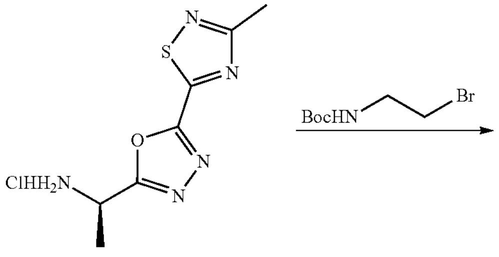

I1

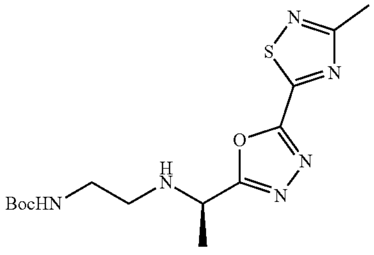

J1

Compound I1 (10 g, 1.0 eq.) and 120 mL of ethyl acetate were added to a 250 mL three-necked flask; a resulting mixture was adjusted to a pH of 8-9 by using a 2% sodium hydroxide solution under stirring, and separated to obtain an aqueous phase; and the aqueous phase was extracted once with 50 mL of ethyl acetate. The combined organic phase was concentrated to dryness to obtain a free base of compound I1. 80 mL of acetonitrile, N-Boc-Bromoethylamine (10.8 g, 1.2 eq.) and triethylamine (4.9 g, 1.2 eq.) were added, and a resulting mixture was heated to 70-80° C. to react for 16 hours under nitrogen protection. A reacted solution was concentrated to dryness to obtain a crude product, and the crude product was purified by silica gel column chromatography to obtain 12.45 g of compound J1, with a yield of 87% as white solid. The chiral purity was 99.9%.

Example 10

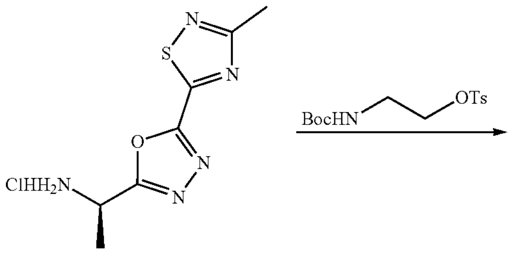

I1

-continued

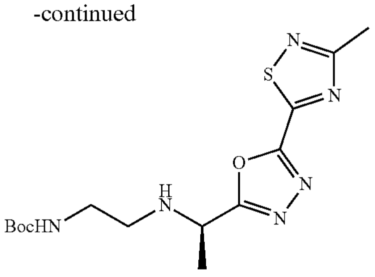

J1

Compound I1 (1 g, 1.0 eq.) and 25 mL of ethyl acetate were added to a 250 mL three-necked flask; a resulting mixture was adjusted to a pH of 8-9 by using a 2% sodium hydroxide solution under stirring, and separated to obtain an aqueous phase; and the aqueous phase was extracted once with 20 mL of ethyl acetate. The combined organic phase was concentrated to dryness to obtain a free base of compound I1. 20 mL of acetonitrile, N-Boc-2-benzenesulfonyloxyethylamine (1.5 g, 1.2 eq.) and triethylamine (0.48 g, 1.2 eq.) were added, and a resulting mixture was heated to 70-80° C. to react for 16 hours under nitrogen protection. A reacted solution was concentrated to dryness to obtain a crude product, and the crude product was purified by silica gel column chromatography to obtain 1.1 g of compound J1, with a yield of 78% as white solid. The chiral purity was 99.9%.

Example 11

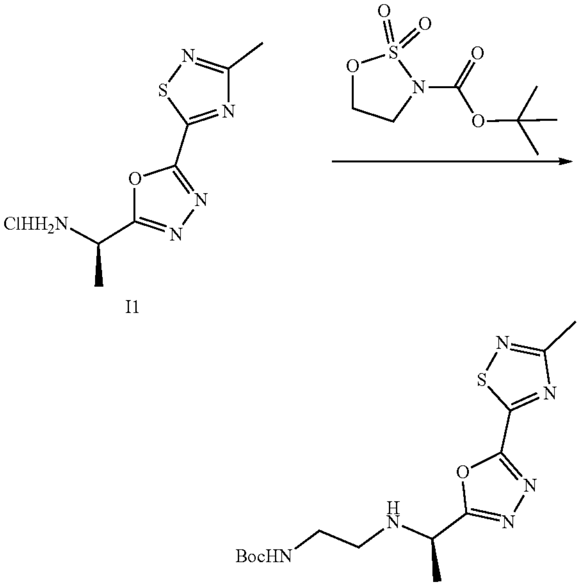

I1

J1

Compound I1 (1 g, 1.0 eq.) and 25 mL of ethyl acetate were added to a 250 mL three-necked flask; a resulting mixture was adjusted to a pH of 8-9 by using a 2% sodium hydroxide solution under stirring, and separated to obtain an aqueous phase; and the aqueous phase was extracted once with 20 mL of ethyl acetate. The combined organic phase was concentrated to dryness to obtain a free base of compound I1. 20 mL of acetonitrile, 1,2,3-oxathiazolidine-3-Boc-2,2-dioxide (1.1 g, 1.2 eq.) and triethylamine (0.48 g, 1.2 eq.) were added, and a resulting mixture was heated to 50-60° C. to react for 16 hours under nitrogen protection. A reacted solution was concentrated to dryness to obtain a crude product, and the crude product was purified by silica gel column chromatography to obtain 1.2 g of compound J1, with a yield of 84% as white solid. The chiral purity was 99.9%.

Example 12

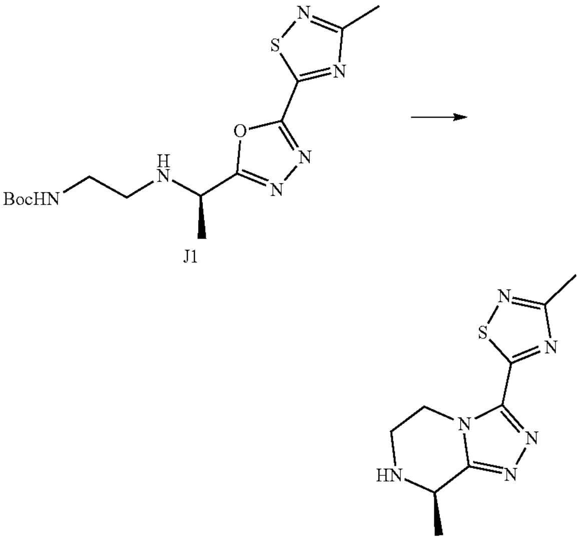

J1

A0

Compound J1 (10 g, 1.0 eq.) and 40 mL of ethyl acetate were added to a 250 mL three-necked flask, a temperature was kept between 20-30° C., and a solution of hydrogen chloride in dioxane (4 M, 40 mL) was added dropwise. After dropwise addition, a resulting mixture was stirred for 2 hours at a holding temperature. A reacted solution was concentrated to dryness, then 50 mL of methanol and triethylamine (8.6 g, 3 eq.) were added, and heated to 50-60° C. to react for 1 hour. A reacted solution was concentrated to dryness to obtain a crude product, and the crude product was purified by silica gel column chromatography to obtain 6.2 g of compound A0, with a yield of 93% as white solid. The chiral purity was 99.2%.

LCMS: [M+1]=237;

$^1$HNMR ($CDCl_3$) δ4.68 (m, 1H), 4.28 (m, 2H), 3.50 (m, 1H), 3.25 (m, 1H), 2.76 (s, 3H), 2.76 (s, 3H), 1.72 (d, 3H).

Example 13

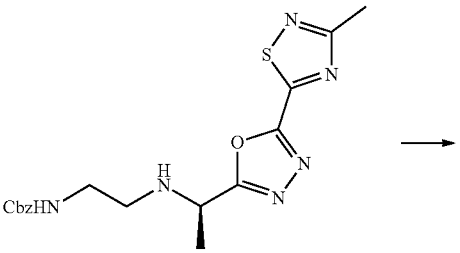

J2

-continued

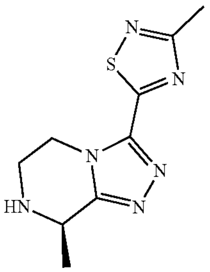

A0

Compound J1 (2.1 g, 1.0 eq.) and 20 mL of acetonitrile were added to a 100 mL three-necked flask, a temperature was kept between 20-30° C., and trimethyliodosilane (4.0 g, 4 eq.) was added dropwise. After dropwise addition, a resulting mixture was stirred for 30 minutes at a holding temperature. Then 20 mL of methanol was added, triethylamine (2.5 g, 5 eq.) was added dropwise, and a resulting mixture was heated to 50-60° C. to react for 4 hours. A reacted solution was concentrated to dryness to obtain a crude product, and the crude product was purified by silica gel column chromatography to obtain 0.94 g of compound A0, with a yield of 80% as nearly white solid. The chiral purity was 99.0%.

Example 14: Synthesis of Fezolinetant

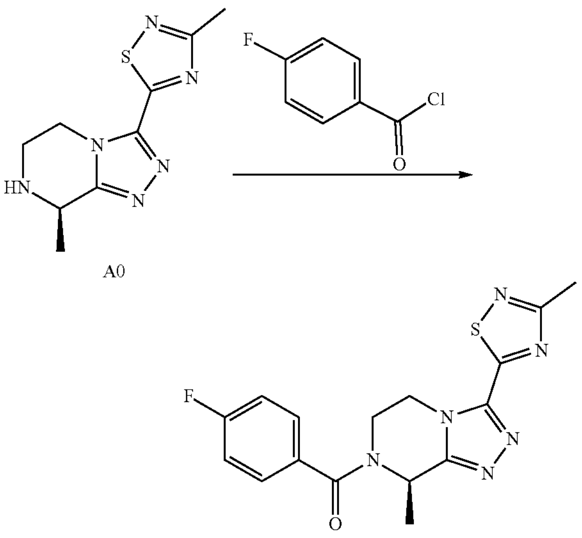

A0

Fezolinetant

Compound A0 (8 g, 1.0 eq.), 80 mL of dichloromethane, and triethylamine (5.1 g, 1.5 eq.) were added to a three-necked flask, cooled to a temperature of 0-10° C., and then 4-fluorobenzoyl chloride (5.9 g, 1.1 eq.) was added dropwise. After dropwise addition, a resulting mixture was stirred for 30 minutes at a holding temperature. A reacted solution was washed with water and a saturated saline solution, respectively. An organic phase was concentrated to dryness, a crude product was recrystallized from ethanol and water to obtain 9.8 g of Fezolinetant, with a yield of 81% as nearly white solid. The HPLC purity was 99.6%, and the chiral purity was 99.9%.

LCMS: [M+1]=359;

$^1$HNMR ($CDCl_3$) δ7.51 (m, 2H), 7.16 (m, 2H), 5.77 (m, 1H), 4.90 (m, 1H), 4.62 (m, 1H), 4.28 (m, 1H), 3.55 (m, 1H), 2.75 (s, 3H), 1.75 (d, 3H).

Comparative Example 1

Compared to Example 1, only N-methylmorpholine was replaced by triethylamine.

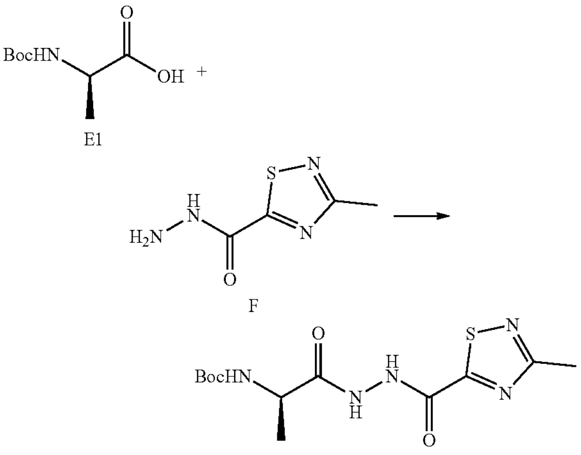

E1

F

G1

Compound E1 (5.0 g, 1.0 eq.), triethylamine (3.2 g, 1.2 eq.) and 50 mL of tetrahydrofuran were added to a 100 mL three-necked flask, and cooled to a temperature of 0° C. under nitrogen protection. Temperature inside the reaction flask was controlled to between −10° C. and 10° C., and isobutyl chloroformate (3.8 g, 1.05 eq.) was added dropwise. After dropwise addition, a resulting mixture was stirred for 20 minutes at a holding temperature, and compound F (4.2 g, 1.0 eq.) was added in batches. After adding the compound F, a resulting mixture was stirred for 10 minutes at a holding temperature. 10% aqueous citric acid solution was added. Tetrahydrofuran was removed by concentration under reduced pressure, dichloromethane was added for extraction for twice, and the obtained organic phase was concentrated to obtain crude product. The crude product was subjected to silica gel column chromatography to obtain 6.5 g of compound G1, with a yield of 75% as light yellow solid. The chiral purity was 99.9%.

Comparative Example 2

Compared to Example 1, the condensing agent was carbonyl diimidazole, specifically:

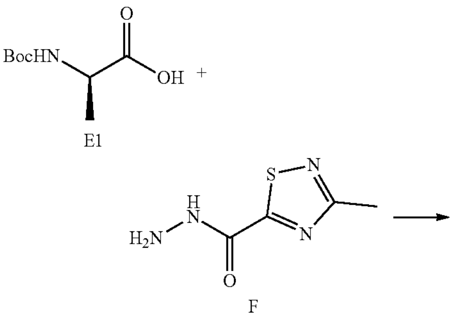

E1

F

-continued

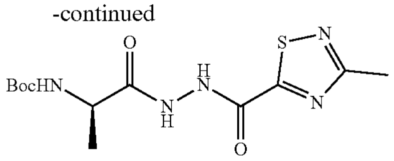

G1

Compound E1 (5.0 g, 1.0 eq.) and 50 mL of acetonitrile were added to a 100 mL three-necked flask, and cooled to a temperature of 0° C. under nitrogen protection. Temperature inside the reaction flask was controlled to between 0° C. and 10° C., and carbonyl diimidazole (4.7 g, 1.1 eq.) was added in batches. After adding carbonyl diimidazole, a resulting mixture was stirred for 30 minutes at a holding temperature, and compound F (4.2 g, 1.0 eq.) was added in batches. After adding compound F, a resulting mixture was stirred for 10 minutes at a holding temperature. Acetonitrile was removed by concentration under reduced pressure, dichloromethane was added, and a 10% aqueous citric acid solution was used for washing. The obtained organic phase was concentrated to obtain a crude product. The crude product was subjected to silica gel column chromatography to obtain 6.2 g of compound G1, with a yield of 72% as light yellow solid. The chiral purity was 98.2%.

Comparative Example 3

Compared to Example 1, the temperature for reaction and the time for reaction were changed, specifically:

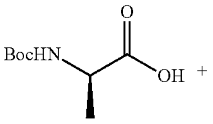

E1

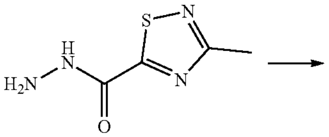

F

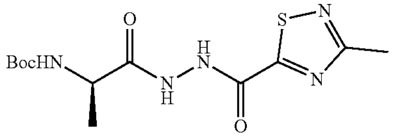

G1

Compound E1 (5.0 g, 1.0 eq.), N-methylmorpholine (3.2 g, 1.2 eq.) and 50 mL of tetrahydrofuran were added to a 100 mL three-necked flask, and cooled to a temperature of 0° C. under nitrogen protection. Temperature inside the reaction flask was controlled to between 20° C. and 30° C., and isobutyl chloroformate (3.8 g, 1.05 eq.) was added dropwise. After dropwise addition, a resulting mixture was stirred for 20 minutes at a holding temperature, and compound F (4.2 g, 1.0 eq.) was added in batches. After adding the compound F, a resulting mixture was stirred for 10 minutes at a holding temperature. A 10% aqueous citric acid solution was added. Tetrahydrofuran was removed by concentration under reduced pressure, dichloromethane was added for extraction for twice, and the obtained organic phase was concentrated to obtain a crude product. The crude product was subjected to silica gel column chromatography to obtain 7.2 g of compound G1, with a yield of 83% as light yellow solid. The chiral purity was 97.5%.

Comparative Example 4

Compared to Example 2, the condensing agent was phosphorus oxychloride.

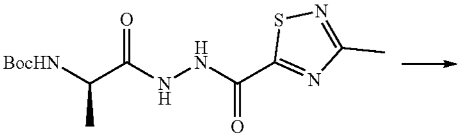

G1

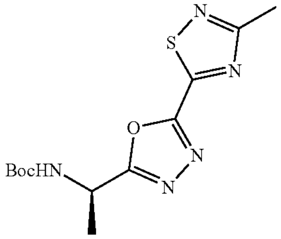

H1

Compound G1 (5.0 g, 1.0 eq.), triethylamine (7.7 g, 5 eq.), and dichloromethane were added to a 1000 mL three-necked reaction flask, and cooled to a temperature of 0-10° C. under nitrogen protection. Phosphorus oxychloride (3.5 g, 1.5 eq.) was added dropwise at a holding temperature. After dropwise addition, a resulting mixture was heated and refluxed to react for 3 hours. A reacted solution was added to 200 mL of icy water for separating an organic phase, washed with a 5% sodium bicarbonate solution, and dried with saturated sodium chloride. The organic phase was concentrated to dryness, and then purified by silica gel column chromatography to obtain 1.5 g of compound H1, with a yield of 32% as white solid. The chiral purity was 99.9%.

Comparative Example 5

Compared to Example 7, the adding amount of raw material was changed, specifically:

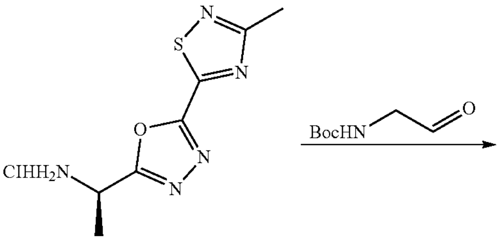

I1

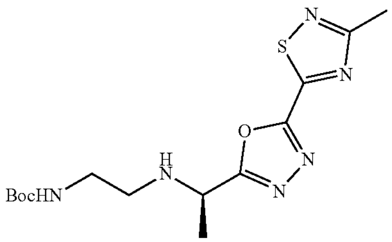

J1

Compound I1 (5 g, 1.0 eq.), Boc aminoacetaldehyde (4.8 g, 1.5 eq.) and 70 mL of dichloromethane was added to a 250 mL three-necked flask, and cooled to a temperature of 0-10° C. under nitrogen protection. Sodium triacetoxyborohydride (8.6 g, 2.0 eq.) was added in batches at a holding temperature. After dropwise addition, a resulting mixture was stirred for 2 hours at room temperature. A reacted solution was washed with a 5% sodium bicarbonate solution and a saturated saline solution, respectively. The organic phase was concentrated to dryness to obtain a crude product, and the crude product was purified by silica gel column chromatography to obtain 5.1 g of compound J2, with a yield of 71% as white solid. The chiral purity was 99.9%.

Comparative Example 6

Compared to Example 12, the solvent for condensation reaction was changed, specifically:

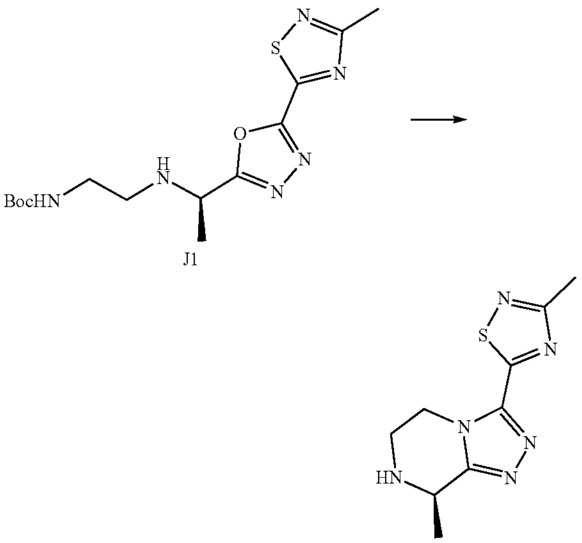

J1

A0

Compound J1 (10 g, 1.0 eq.) and 40 mL of dioxane were added to a 250 mL three-necked flask, a temperature was kept between 20-30° C., and a solution of hydrogen chloride in dioxane (4 M, 40 mL) was added dropwise. After dropwise addition, a resulting mixture was stirred for 2 hours at a holding temperature. A reacted solution was concentrated to dryness, then added with 50 mL of ethyl acetate and triethylamine (8.6 g, 3 eq.), and heated to 50-60° C. to react for 1 hour. A reacted solution was cooled to room temperature, 40 mL of saturated sodium bicarbonate was added for washing, a aqueous phase was separated and washed once with 30 mL of ethyl acetate. The combined organic phase was concentrated to dryness, 40 mL of n-heptane was added, and a resulting mixture was slurried to obtain 6.0 g of compound A0, with a yield of 90% as nearly white solid. The chiral purity was 99.3%.

Finally, it should be noted that the above content is only used to illustrate the technical solution of the present disclosure, instead of limiting the scope of protection of the present disclosure. Simple modifications or equivalent replacements made by those ordinary skilled in the art to the technical solution of the present disclosure do not depart from the essence and scope of the technical solution of the present disclosure.

What is claimed is:

1. A compound of Formula I, having a following structure:

Formula I

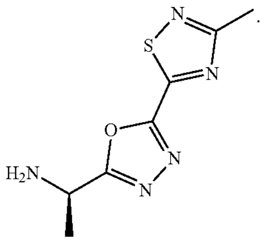

2. A method for preparing the compound of Formula I according to claim 1, comprising:

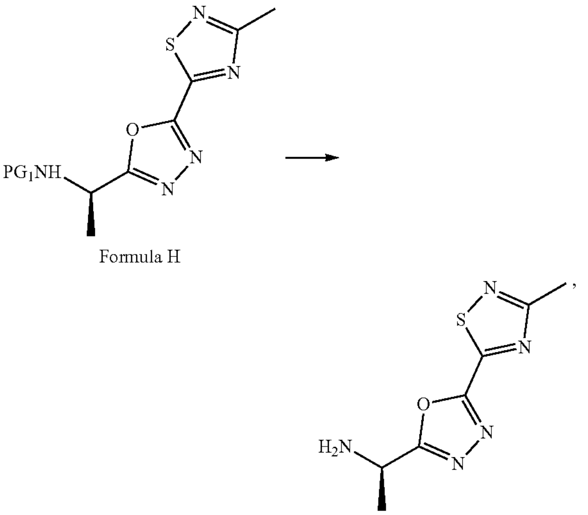

Formula H

Formula I deprotecting a compound of Formula H to obtain the compound of Formula I or a salt thereof;

wherein $PG_1$ is a protective group; and the $PG_1$ is tert-butoxycarbonyl, benzyloxycarbonyl or trifluoroacetyl.

3. The method according to claim 2, wherein the salt is a hydrochloride salt, a hydrogen bromide salt, a p-toluenesulfonic acid salt, or a methylsulfonic acid salt.

* * * * *